(12) United States Patent
Kahlman et al.

(10) Patent No.: US 8,828,740 B2
(45) Date of Patent: Sep. 9, 2014

(54) RAPID AND SENSITIVE BIOSENSING

(75) Inventors: Josephus Arnoldus Henricus Maria Kahlman, Eindhoven (NL); Rachel Estelle Thilwind, Eindhoven (NL); Menno Willem Jose Prins, Eindhoven (NL); Mischa Megens, Eindhoven (NL); Reinhold Wimberger-Friedl, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1579 days.

(21) Appl. No.: 11/814,826

(22) PCT Filed: Jan. 30, 2006

(86) PCT No.: PCT/IB2006/050322
§ 371 (c)(1),
(2), (4) Date: Jul. 26, 2007

(87) PCT Pub. No.: WO2006/079998
PCT Pub. Date: Aug. 3, 2006

(65) Prior Publication Data
US 2008/0191688 A1  Aug. 14, 2008

(30) Foreign Application Priority Data
Jan. 31, 2005 (EP) .................................. 05100618

(51) Int. Cl.
*G01N 33/553* (2006.01)
*G01N 27/74* (2006.01)
*G01N 33/543* (2006.01)

(52) U.S. Cl.
CPC ............ *G01N 27/745* (2013.01); *G01N 33/553* (2013.01); *G01N 33/54333* (2013.01)
USPC ........................................ 436/526; 435/287.2

(58) Field of Classification Search
CPC ..................................................... G01N 33/553
See application file for complete search history.

(56) References Cited

U.S. PATENT DOCUMENTS 5,872,384 A * 2/1999 Gabara ......................... 257/421
5,929,637 A * 7/1999 Taguchi et al. ............... 324/306

(Continued)

FOREIGN PATENT DOCUMENTS

EP          1316809 A2 *  6/2003
JP       1989273586 A    11/1989

(Continued)

OTHER PUBLICATIONS

Schmitz et al "The Role of Orientation Constraints and Rotation Diffusion in Biomolecular Solution Kinetics" J. Phys. Chem., vol. 76, 1972, pp. 537-545.
Graham et al "Single Magnetic Microsphere Placement and Detection on-Chip using Current Line Designs with Integrated Spin Valve Sensors: Biotechnological Applications" Journal of Applied Physics, vol. 91, No. 10, May 2002 pp. 7787-7788.

(Continued)

*Primary Examiner* — Chris L Chin

(57) ABSTRACT

A sensor device (15) for detecting magnetic particles (13) has a binding surface (40) with binding sites thereon and includes at least one sensor element (23) for detecting the presence of magnetic particles (13), an element or elements for attracting magnetic structures having at least one magnetic particle (13) toward and onto the binding surface (40) of the sensor device (15), and an element or elements for re-arranging and randomizing the position of individual magnetic particles (13) with respect to the binding sites on the binding surface (40) to give binding sites on all individual particles (13) a substantial probability to have a contact time with binding sites on the binding surface (40). With such sensor device (15), the speed of detection of target molecules in a fluid is enhanced.

13 Claims, 12 Drawing Sheets

(56) References Cited

U.S. PATENT DOCUMENTS

| | | | |
|---|---|---|---|
| 6,290,839 B1 * | 9/2001 | Kayyem et al. | 205/777.5 |
| 2002/0001855 A1 | 1/2002 | Prentiss | |
| 2003/0012693 A1 | 1/2003 | Otillar | |
| 2003/0095897 A1 | 5/2003 | Grate | |
| 2004/0009614 A1 * | 1/2004 | Ahn et al. | 436/526 |
| 2004/0235197 A1 | 11/2004 | Kotitz | |
| 2005/0106758 A1 | 5/2005 | Fukumoto | |

FOREIGN PATENT DOCUMENTS

| | | |
|---|---|---|
| WO | 03054523 A2 | 7/2003 |
| WO | WO 2005019263 A1 * | 3/2005 |

OTHER PUBLICATIONS

Ferreira et al "Biodetection using Magnetically Labeled Biomolecules and Arrays of Spin Valve Senros (invited)" Journal of Applied Physics, vol. 93, No. 10, May 2003, pp. 7281-7286.

Baudry et al "Bio-Specific Recognition and Applications: from Molecular to Colloidal Scales" Journal of Physics Condensed Matter, vol. 16 (2004) R469-R480.

Perrin et al "Immunomagnetic Concentration of Antigens and Detection based on a Scanning Force Microscopic Immunoassay" Journal of Immunological Methods, vol. 224, (1999) pp. 77-87.

* cited by examiner

RAPID AND SENSITIVE BIOSENSING

The present invention relates to sensors, especially biosensors and more particularly to methods for a magnetically actuated 'attracting' and/or 'binding' step in a biosensing process using such biosensors.

Medical diagnostics, both in the central laboratory and at the bedside, is characterized by a drive towards integration and automation. The reason for this is that tests need to be easy to perform, in a reliable and cost effective way, with minimum human intervention. At the same time there is an ever-increasing need for higher sensitivity and specificity of detection.

Magnetic biochips have been proposed as a new means to sensitively detect low concentrations of target molecules in body fluids for diagnostics. Such magnetic biochips have promising properties for bio-molecular diagnostics, in terms of sensitivity, specificity, integration, ease of use and costs. For example, sensitive magneto-resistive magnetic field sensors, such as GMR magnetic field sensors, can be combined with suitable biochemistry to selectively attach magnetic beads, resulting in a miniaturized biosensor that is suitable for detection in an array format. The sensitivity and specificity of rapid tests is usually provided by dedicated capture of probe molecules, e.g. a high-affinity antibody-antigen combination. In such an immunoassay, the target molecules become sandwiched between antibodies on a solid support and a label that is detected by the sensor. Conventionally this label is a fluorophore, and a plate reader is used for detection. In the most sensitive assays, the test is performed on magnetic bead carriers that can be actuated so the reaction rate is no longer limited by diffusion and the test is speeded up. Magnetic detection naturally combines actuation and detection by using the magnetic beads as both label and carrier. Besides this natural integration, magnetic labelling has several other advantages: body liquids do show autofluorescence, but are by nature hardly magnetic, which helps to improve the detection limit. Magnetic detection of magnetic particles requires no expensive optics, yet is fast and sensitive, and furthermore, it is well suited for miniaturized diagnostic sensing, due to the direct availability of electronic signals and the small size of the required instrumentation.

The aim of a biosensor is to detect and quantify the presence of a biological molecule in a sample, usually a solution. Desired attributes are high sensitivity, high specificity, and high speed. Furthermore, the biosensor is preferably of low cost and it should be reliable and easy to use.

For many decades magnetic particles have been used in biology for separation, extraction and purification of biological materials. In recent years, biosensors based on the use of magnetic particles for actuation as well as detection have started to develop. In these studies, magnetic particles are detected by optical methods, electric means, coils or magneto-resistive sensors. Actuation of the particles is used for stringency, to concentrate the particles near the detection surface or to enhance particle-to-particle binding.

For high sensitivity and high speed in a sandwich assay, the following protocol may be attempted:
Disperse: Mix beads into the fluid sample.
Catch: Let targets bind to beads.
Attract: Bring beads toward the binding surface of the sensor device.
Bind: Let beads form biological bonds to the binding region or binding sites of the sensor. The binding surface of the sensor has a portion which is chemically and/or biochemically prepared to enable binding of particles, in particular via selective biochemical bonds. In the case of a sandwich format, the biochemical bond involves at least the following elements: an area on the sensor binding surface, a first binding entity, a target, a second binding entity, and the bead.
Stringency (i.e. selective removal): Remove unbound and weakly bound beads from the binding surface of the sensor device, either magnetically or non-magnetically. Determine relative binding forces.

The catching step can be made very fast by providing a high surface-to-volume ratio, i.e. by dispersing many small particles in the solution. However, this is only useful when the other steps can also be made very rapid. Thermal diffusion, however, gives only slow transport of sub-micrometer beads towards the binding surface. The transport can be enhanced by applying magnetic field gradients, e.g. with a permanent magnet [as in Perrin, J. Immun. Meth 224, 77 (1999) for example].

Furthermore, a biosensor comprising an array of sensors, e.g. 100 sensors, based on the magnetic detection of magnetic beads, e.g. superparamagnetic beads, may be used to simultaneously measure the concentration of a large number of different biological molecules (e.g. proteins, DNA) in a solution (e.g. blood). This may be achieved by attaching magnetic beads to target molecule, magnetising these beads with an applied magnetic field and using a Giant Magneto Resistance (GMR) sensor to detect the stray field of the magnetised beads, which stray field is dependent on the concentration. FIG. 1 shows an example of integrated excitation, wherein the magnetic sensor includes current wires 1a and 1b and GMR sensor 4. A current flowing in current wire 1a generates a magnetic field, which magnetises a magnetic bead 2 which is attached to a target molecule 3. Hence, the beads 2 present at a binding surface 6 of the sensor device each develop a magnetic moment m indicated by the field lines 7. The stray field from the magnetic bead 2 introduces an in-plane magnetisation component $H_{ext}$ in the GMR sensor 4, which results in a resistance change $\Delta R_{GMR}(H_{ext})$. In FIG. 1, the in-plane component $H_{ext}$ is indicated by arrow 5.

In order to achieve a short assay time, the magnetic beads 2 have to be magnetically actuated, i.e. by means of magnetic actuation attracted to the binding surface 6. Thereafter, the binding process needs to take place as efficiently as possible. This means that (i) the particles need to be concentrated onto the binding zones with highest detection sensitivity by the sensors, and (ii) that all particles need to have optimum possibilities to form the desired (bio)chemical bonds to the binding surface. A disadvantage of attraction by a large external permanent magnet is that the magnetic particles form large and static aggregates on the surface, which does not give optimum binding conditions to the binding surface. In addition, magnets can give large in-plane magnetic fields 5, which influence the sensitivity of the magnetic sensor due to shifting of the operation point on the non linear R(H) resistance change characteristic of the sensor. Furthermore, the large magnetic fields may de-orientate the sensor and introduce magnetic build-up in the sensor due to its hysteric characteristic.

It is an object of the present invention to provide improved apparatus and methods for biosensing. An advantage of embodiments of the present invention can be optimisation of the 'bind' process, e.g. by increasing the contact efficiency (to maximise the rate of specific biological binding when the bead is close to the binding surface) and/or the contact time (the total time that individual beads are in contact with the binding surface. An advantage of embodiments of the present invention can be enhancing the speed of the detection of target molecules in a fluid when using magnetic particles as labels in a sensor device such as e.g. a magnetic sensor device for the detection of the magnetic particles. An advantage of the present invention is a sensor suitable for high rate biosensing. The methods and apparatus according to embodiments of the present invention allow for the detection of target molecules such as e.g. proteins, antibodies, nucleic acids (e.g. DNA, RNA), peptides, oligo- or polysaccharides or sugars, in fluids, for example, biological fluids, such as saliva, sputum, blood, blood plasma, interstitial fluid or urine, with high sensitivity and specificity.

The above objective is accomplished by a method and device according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

In a first aspect of the present invention, a sensor device, e.g. a magnetic sensor device, for detecting magnetic particles is provided, the sensor device having a binding surface with binding sites thereon and comprising:
 at least one sensor element for detecting the presence of magnetic particles,
 means for attracting magnetic structures toward and onto the binding surface of the sensor device, said magnetic structures comprising at least one magnetic particle, and
 means for re-arranging and randomising the position of individual magnetic particles with respect to the binding sites on the binding surface to give binding sites on all individual magnetic particles a substantial probability to have a contact time with binding sites on the binding surface.

By re-arranging and randomising the position of individual magnetic particles with respect to the binding sites on the binding surface provides an improved binding of the magnetic particles onto the binding sites. The individual magnetic particles may be particles which are part of a multi-particle magnetic structure.

A sensor device according to embodiments of the present invention may furthermore comprise field generating means, in particular magnetic field generating means, adapted for forming multi-particle magnetic structures having a long axis substantially parallel with the binding surface of the sensor device, said multi-particle magnetic structures comprising a plurality of individual magnetic particles.

By forming multi-particle structures having a long axis substantially parallel with the binding surface of the sensor device, a small distance between most of the particles or beads in a multi-particle structure and the binding surface may be achieved, because the multi-particle structures are aligned along the binding surface.

The at least one sensor element preferably may be a magnetic sensor element such as e.g. a GMR, TMR, AMR or Hall sensor element, but it may also be another sensor element such as, for example, an optical sensor element. Hence, instead of magnetic detection of particles, the particles may also be optically detected.

For magnetic particles present in a sample volume, the means for re-arranging and randomising the position of the individual magnetic particles may be adapted such that individual magnetic particles are loosened from the binding surface such that 90% of the individual magnetic particles which are part of a magnetic structure, e.g. an individual particle itself or a multi-particle structure, stay within 10% or less of the sample volume. Hence, during re-arrangement and randomisation, the magnetic particles do not go far from the binding surface in a direction substantially perpendicular to the binding surface. The magnetic particles preferably stay within 100 μgm from the binding surface and more preferably stay within 10 μm from the binding surface in a direction substantially perpendicular to the binding surface. Randomisation of the magnetic particles may be performed e.g. by changing a magnetic gradient in time, in amplitude, in frequency (depending on the amplitude and the magnetic anisotropy of the magnetic particles) or in direction. Alternatively, in order to randomise magnetic particles they may be vibrationally excited or exposed to fluid flow.

The sensor may be in the form of a disposable cartridge with a cartridge reader for providing a read-out from the sensor. The sensor may be partially or wholly integrated onto a semiconductor chip. The field generating means adapted for forming multi-particle magnetic structures may, according to embodiments of the invention, be an on-chip magnetic field generating means, e.g. current wires, or an off-chip magnetic field generating means. The off-chip magnetic field generating means may be a magnetic field generating means present in the disposable cartridge for the biosensor but not on the chip, or it may be present in the cartridge reader.

Preferably the chip and cartridge are made of materials that are suited for low-cost mass-manufacturing, such as organic or inorganic materials, e.g. silicon, glass, plastics, composites, ceramics, etc.

According to embodiments of the invention, multi-particle structures may be chains of magnetic particles, rings of magnetic particles, clusters of magnetic particles or other known multi-particle structures. These structures have a long axis lying essentially in-plane, i.e. an axis lying in a plane. The orientation of the long axis is depending on the orientation of applied magnetic fields. The long axis may be straight or curved.

The means for attracting the magnetic structures, e.g. individual particles or multi-particle structures, toward and onto the binding surface of the sensor device may be an on-chip or an off-chip means. The means for attracting said magnetic structures, e.g. individual particles or multi-particle structures, toward and onto the binding surface of the sensor device may be an on-chip or an off-chip element having a relative permeability larger than one, i.e. the means for attracting said magnetic structures, e.g. individual particles or multi-particle structures, may comprise a fluxguide. The on-chip or off-chip element may be a kind of MEMS (microelectromechanical system) element which may change position or shape in order to vary a magnetic field gradient for attracting the magnetic structures, e.g. individual particles or multi-particle structures, toward and onto the binding surface of the sensor device.

In one particular embodiment of the invention, the means for attracting the magnetic structures, e.g. individual particles or multi-particle structures toward and onto the binding surface of the sensor device may comprise a first current wire and at least one additional current wire. In another embodiment, the means for attracting the magnetic structures, e.g. individual particles or multi-particle structures, may be an array of current wires.

In a second aspect, the invention also provides a method for a biosensing process, the biosensing process comprising detection of magnetic particles by means of a sensor device having a binding surface with binding sites thereon. The method comprises:
 attracting said magnetic structures comprising at least one magnetic particle toward and onto the binding surface of the sensor device, and re-arranging and randomising the position of the individual magnetic particles with respect to the binding sites on the binding surface to give binding sites on all individual magnetic particles a substantial probability to have a contact time with binding sites on the binding surface.

For magnetic particles present in a sample volume, re-arranging and randomising the position of the individual magnetic particles may be adapted such that individual magnetic particles are loosened from the binding surface in such a way that 90% of the individual magnetic particles which are part of a magnetic structure, e.g. an individual particle itself or a multi-particle structure, stay within 10% or less of the sample volume. Hence, during re-arrangement and randomisation, the magnetic particles do not go far from the binding surface in a direction substantially perpendicular to the binding surface. The magnetic particles preferably stay within 100 µm from the binding surface and more preferably stay within 10 µm from the binding surface in a direction substantially perpendicular to the sensor binding surface.

A method according to embodiments of the present invention may furthermore applying a magnetic field adapted for forming multi-particle magnetic structures having a long axis lying substantially parallel with the binding surface of the sensor device, the multi-particle magnetic structures comprising a plurality of individual magnetic particles.

Applying the magnetic field for generating multi-particle structures may be performed by applying a chain-forming magnetic field for forming chains of magnetic particles.

According to embodiments of the invention, attracting the magnetic structures, e.g. individual particles or multi-particle structures, toward and onto the sensor binding surface may be performed by applying an on-chip or an off-chip magnetic field. In some embodiments, attracting the magnetic structures, e.g. individual particles or multi-particle structures, may be performed by applying a magnetic field gradient in a direction substantially perpendicular to the binding surface of the sensor device.

The sensor device, if it is a magnetic sensor device, may have at least one magnetic sensor element with a sensitive direction, and attracting the magnetic structures, e.g. individual particles or multi-particle structures, toward and onto the binding surface may be performed by applying a magnetic field in the sensitive direction of the magnetic sensor element. In other embodiments according to the invention, the sensor device may comprise at least a first and second current wire and attracting the magnetic structures, e.g. individual particles or multi-particle structures, toward and onto the binding surface may be performed by sending a first current through the first current wire and sending a second current through the second current wire. The first and the second current may be equal in magnitude. They may have opposite directions. In still further embodiments, attracting the magnetic structures, e.g. individual particles or multi-particle structures, toward and onto the binding surface may be performed by an array of current wires.

In other embodiments of the invention, generating multi-particle structures having a long axis essentially parallel to the binding surface may comprise:
  applying a first magnetic field for forming out-of-plane multi-particle structures, i.e. multi-particle structures which are not lying essentially parallel to the binding surface, and
  subsequently applying a second magnetic field for orienting the multi-particle structures so as to have their long axis essentially in plane substantially parallel with the binding surface of the sensor device.

The magnetic field may subsequently be rotated to get maximum contact between individual magnetic particles and the binding surface.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
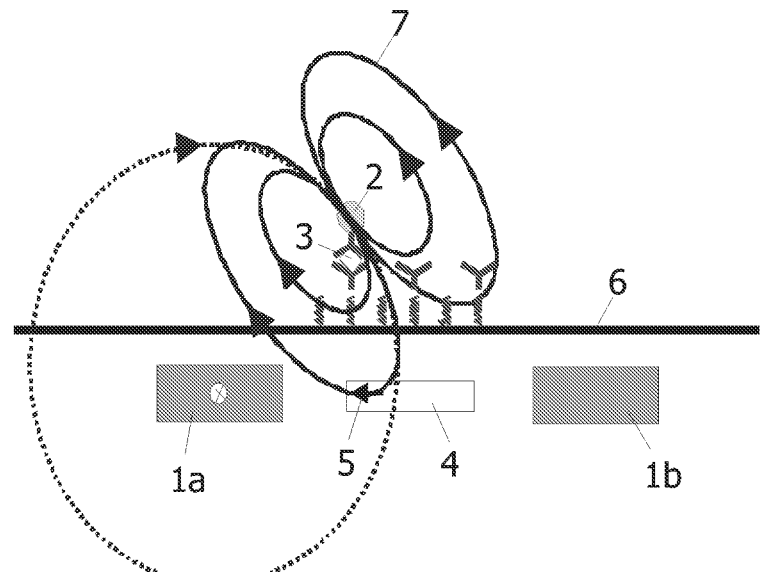
FIG. 1 illustrates a magnetic sensor according to the prior art.

In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The present invention provides a device and a method for biosensing. An advantage of the present invention can be improving the speed of a biosensing process performed by using a sensor device, e.g. but not limited to a magnetic sensor device. In biosensing processes using a magnetic sensor device, magnetic particles or beads are directly or indirectly attached to target molecules such as e.g. proteins, antibodies, nucleic acids (e.g. DNR, RNA), peptides, oligo- or polysaccharides or sugars, small molecules, hormones, drugs, metabolites, cells or cell fractions, tissue fractions. These molecules are to be detected in a fluid, which can be the original sample or can already have been processed before insertion into the biosensor (e.g. diluted, digested, degraded, biochemically modified, filtered, dissolved into a buffer). The original fluids can be for example, biological fluids, such as saliva, sputum, blood, blood plasma, interstitial fluid or urine, or other fluids such as drinking fluids, environmental fluids, or a fluid that results from sample pre-treatment. The fluid can for example comprise elements of solid sample material, e.g. from biopsies, stool, food, feed, environmental samples.

The surface of the sensor device may be modified by attaching molecules to it, which are suitable to bind the target molecules which are present in the fluid. The surface of the sensor can also be provided with organisms (e.g. viruses or cells) or fractions of organisms (e.g. tissue fractions, cell fractions, membranes). The surface of biological binding can be in direct contact with the sensor chip, but there can also be a gap between the binding surface and the sensor chip. For example, the binding surface can be a material that is separated from the chip, e.g. a porous material. Such a material can be a lateral-flow or a flow-through material, e.g. consisting of microchannels in silicon, glass, plastic, etc. The binding surface can be parallel to the surface of the sensor chip. Alternatively, the binding surface can be under an angle with respect to, e.g. perpendicular to, the surface of the sensor chip.

Before the magnetic particles or the target molecules/magnetic particles-combination can be bound to the surface of the sensor device, they have to be attracted towards that surface. Embodiments of the present invention now provide a method for improving the speed of biosensing by improving the speed of at least one of the 'attracting' and/or the 'binding' phases in the assay protocol as described in the background section. According to embodiments of the present invention, the attracting phase may be speeded up by magnetic actuation of target molecules/magnetic particles combinations. The 'bind' process may be optimised by increasing the contact efficiency (to maximise the rate of specific biological binding when the bead is close to the binding surface) as well as the contact time (the total time that individual beads are in contact with the binding surface.

In a first aspect, not explicitly illustrated in the drawings, the present invention proposes the use of means for re-arranging and randomizing the position of individual magnetic particles with respect to the binding sites on the binding surface, in order to give binding sites on all individual particles a substantial probability to have a contact time with binding sites on the binding surface, and thus in order to optimise the bind process. It has to be noted that magnetic particles can be used in various types of assays, e.g. a binding or unbinding assay, sandwich assay, displacement assay, inhibition assay, or competition assay. In the following, focus will be laid on a binding assay, more in particular a sandwich assay, but the described methods are not limited to this assay type.

In a biosensor assay, the 'attract' and 'bind' phases need to be made as efficient and as fast as possible. In the 'attract' phase the beads are concentrated from the bulk of the fluid to a zone near the sensor binding surface. The time needed to attract the particles toward the binding surface should be as low as possible, lower than 30 minutes, preferably lower than 10 minutes, and more preferred lower than 1 minute.

In the 'bind' phase, the resulting bead ensemble is brought even closer to the binding surface in a way to optimise the occurrence of desired (bio)chemical binding to the capture or binding area on the sensor, i.e. the area where there is a high detection sensitivity by the sensors, e.g. magnetic sensors, and a high biological specificity of binding. It is not trivial to optimise the 'bind' process. Therefore, there is a need to increase the contact efficiency (to maximise the rate of specific biological binding when the bead is close to the binding surface) as well as the contact time (the total time that individual beads are in contact with the binding surface).

First, the contact efficiency will be discussed. The contact efficiency deals with the contact between the surface of the beads that are closest to the sensor and the surface of the binding region on the sensor. Ideally, the distance between the biological molecules on the surface of the beads and the biological molecules on surface of the binding region of the sensor should be in the order of the size of the biological molecules, for example, a distance of 0-100 nm.

For a single bead near a surface and exposed to a magnetic field gradient, the distance of approach ξ can be estimated by comparing the thermal fluctuations with the magnetic force:

$$F\xi = m\nabla B\xi = kT \Rightarrow \xi = \frac{kT}{m\nabla B} \qquad (6)$$

A magnetic field gradient ∇B thus has to be generated in order to attract the particles or beads toward the binding surface. The larger the magnetic field gradient ∇B, and thus the larger the force F on the beads, the smaller the distance of approach ξ. Magnetic field gradients ∇B may be generated in different ways. For example, by an external means (e.g. an external magnet or coil). An external coil may, for example, generate a magnetic field gradient of 25 T/m. Magnetic field gradients may also be generated by at least one on-chip current wire. In that case the gradient may be estimated from:

$$\frac{dB}{dR} = \frac{\mu_0 I}{2\pi r^2} \qquad (7)$$

wherein I is the current through the current wire and r is the distance between the magnetic bead and the current wire. As an example, a current of 10 mA at a distance of 0.5 μm from the bead may generate, at the level of the bead, a field gradient of $8.10^3$ T/m.

As another example, the magnitude of the magnetic field gradient in the vicinity of magnetic material embedded in the sensor surface is calculated. The example is taken that magnetic beads are embedded in the material. The magnitude of the magnetic field gradient at a distance r away from the centre of a spherical bead with moment m is approximately given by:

$$\nabla B \approx \frac{\mu_0}{4\pi} \frac{6m}{r^4} \qquad (8)$$

For simplicity, the angle dependency of the gradient, which may give differences of a factor two, has been ignored in equation (8). For example, a 300 nm bead with magnetic moment $m=10^{-16}$ Am$^2$ may generate a gradient of about $2.10^3$ T/m at a distance of 400 nm.

For example, assuming a field gradient of $10^3$ T/m. From equation (6) it can be calculated that for a magnetic moment m, resulting from a single bead structure (or from a multi-bead structure as in the second aspect of the present invention), of $10^{-15}$ Am$^2$ or more, a distance of approach or attraction ξ can be achieved of 4 nm (if $m=10^{-15}$ Am$^2$) or less (if m is larger than $10^{-15}$ Am$^2$) at room temperature. This means that very small distances can in principle be achieved already by using practical magnetic field gradients, e.g. in the range between 10 T/m and 10000 T/m, so that efficient biological binding can take place.

Secondly, the contact time will be discussed. When a large number of beads or particles is attracted to the binding surface of a sensor device and the complete binding surface becomes covered with magnetic particles, the magnetic structure thus formed will be very dense but also static and rigid. Due to translational constraints, a large fraction of particles cannot reach the binding surface and will not have a chance to form a desired specific biochemical bond. This causes a loss of signal in the biosensor and thus a false reading or an unnecessarily long assay time.

The inventors have realised that individual beads have a freedom of rotation. For example, superparamagnetic beads have a very weak magnetic anisotropy, so a very weak coupling exists between the magnetic moment and the physical orientation of the particle. Thermal energy causes rotation of the magnetic beads (rotational diffusion) and as a result the beads will expose a significant part of their surface area to the binding surface. The surface-to-surface exposure will allow the formation of specific biochemical bonds.

According to the present invention, the magnetic particles may be randomised regularly or irregularly, e.g. by removing and re-applying the magnetic fields attracting the individual magnetic particles to the binding surface of the sensor device, or by rotational excitation of the beads, or by the application of fluid motion such as stirring or acoustic vibrations. With randomised is meant that magnetic particles which are attracted to the binding surface but which do not bind to the binding surface are shortly moved away from the binding surface but never get very far from the binding surface, i.e. they stay within a short distance from the binding surface in the z-direction, i.e. a direction perpendicular to the binding surface. Preferably, they stay within 100 μm from the binding surface and more preferably they stay within 10 μm from the binding surface in a direction substantially perpendicular to the binding surface. According to the invention, the particles are moved away from the binding surface such that 90% of the magnetic particles which are attracted to the binding surface stay within 10% or less of the sample volume. Particles do not disperse back into the complete sample volume. The repeated attractions and randomisations ensure that biological material coupled to magnetic beads have a high probability to be at least once in contact with the binding sites on the binding surface of the sensor device during the total assay, i.e. that all targets have a substantial probability to have a contact time with binding sites on the binding surface of the sensor device.

The magnetic particles or beads are thus attracted toward and onto the binding surface by means of a magnetic field gradient.

The assay should be designed to achieve maximum specific binding (by attraction of the beads toward the binding surface) and minimum hindering of binding (all beads should have a significant probability to interact with binding sites on the binding surface of the sensor device), and minimum unwanted unbinding (due to forces breaking the desired bonds between beads and binding surface).

As explained, rotation of magnetic particles may be used to optimise the exposure rate and binding rate in a biochemical assay. The rotation can be caused by thermal energy but can also be generated or enhanced by time-varying applied fields. Firstly, when magnetic particles are present in solution, rotation of these magnetic particles can enhance the interaction and binding rate between the biological material in solution and the surface of the magnetic particles. This, for example, applies to the fishing or catching phase in an assay, wherein magnetic particles are used to bind to specific biological material in a sample solution and/or to extract this material. Secondly, when magnetic particles are rotated with respect to another body, for example the surface of a biochip or the surface of a cell, the interaction and binding rate between the label and the other body can be enhanced. The increase of the binding rate may particularly be of importance when the surface area of the label is large with respect to the size of the relevant molecular binding region on the magnetic particle. This is, for example, the case in low-concentration assays, when a catching or fishing step yields magnetic particles with only very little biological material of interest on the magnetic particle surface. For reference, some calculations on the role of orientation and rotation in biomolecular kinetics can be found in "K. S. Schmitz and J. M. Schurr: 'The role of orientation constraints and rotation diffusion in biomolecular solution kinetics', J. Phys. Chem., vol. 76, p. 534 (1972)".

The ideal rotation speed is given by an optimal binding rate at acceptable unbinding rate for the biochemical bond that needs to be formed in the given assay time. In other words, the rotation is optimised for sensitivity as well as specificity. To avoid removal of the desired specific bindings, the applied forces need to be below 1 nN.

In a second aspect the present invention furthermore proposes the use of multi-particle magnetic structures, such as e.g., but not limited thereto, chains or columns of magnetic particles or beads, e.g. for achieving enhanced speed in biosensing. More particularly, according to the invention, multi-particle structures are used to increase the speed of the process steps 'attract' and/or 'bind' in a biosensing protocol. It has to be noted that magnetic particles can be used in various types of assays, e.g. a binding or unbinding assay, sandwich assay, displacement assay, inhibition assay, or competition assay. In the following, focus will be laid on a binding assay, more in particular a sandwich assay, but the described methods are not limited to this assay type.

An advantage of using multi-particle structures is that individual particles inside the structures have a higher magnetic moment due to the reduced demagnetising fields. In addition, the total magnetic moments of such structures, and therefore also the magnetic forces, are larger than in case of individual particles. The force that can be applied to a magnetic multi-particle structure is given by equation (1):

$$F = \nabla(m \cdot B) \approx m \nabla B \tag{1}$$

wherein m is the magnetic moment of the multi-particle structure, B the applied magnetic field and $\nabla B$ the gradient of the applied magnetic field. A chain of, for example, 100 particles can experience an approximately 100-fold higher force than a single particle or bead due to the higher total magnetic moment m of the multi-particle structure. Multi-particle structures according to the second aspect of the present invention may comprise a combination of large and small particles but may also be structures comprising particles with similar size. Typically, multi-particle structures may comprise 5 to several 1000 magnetic particles or beads, but even higher numbers are also possible.

In the following description the second aspect of the invention will be described by means of chains or columns of magnetic particles. It has, however, to be understood that this is only for the ease of explanation and that this is not limiting to the invention. Other multi-particle structures can also be used according to the second aspect of the invention, e.g. clusters of magnetic particles, or single or multiple loops, or rings of magnetic particles.

Figure 2:
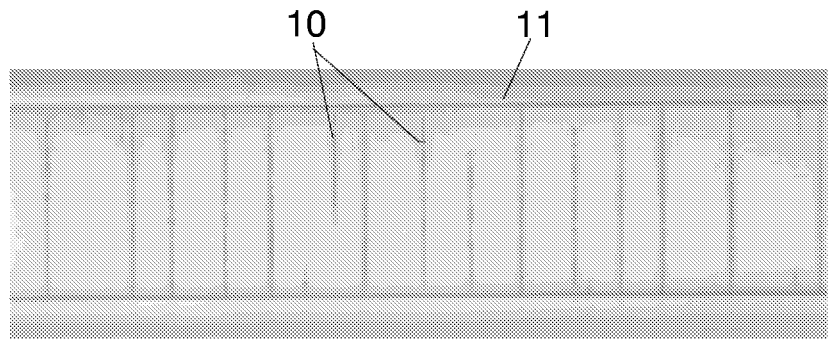
FIG. 2 illustrates magnetic bead interactions and chain formation in the presence of a uniform magnetic field.

Thus, one example of a multi-particle structure which can be used according to the second aspect of this invention is a chain 10 of magnetic particles or beads. It is known that magnetic particles or beads form chains 10 when the inter-bead magnetic forces exceed the thermal motion. Magnetising magnetic particles or beads in a magnetic field has the effect of inducing a dipole-dipole interaction between neighbouring beads, which, if the interaction energy exceeds the thermal energy of the particles, results in the formation of chains 10 of magnetic particles in the direction of the magnetic field lines. Over time, the chains 10 interact with each other to form columns. In, for example, a uniform magnetic field without field gradients, the chains and columns can arrange in regular patterns due to repulsion caused by the dipole moments. This is illustrated in FIG. 2, which shows magnetic bead interactions and formation of chains 10 in the presence of a uniform magnetic field in a square capillary tube 11 of 50 μm [Baudry et al., J. Phys. Cond. Matt. 16, R469 (2004)].

Figure 25:
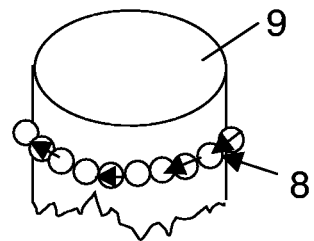
FIG. 25 illustrates formation of a loop or ring of magnetic particles.

The multi-particle structures that are formed are determined by the applied field pattern, the duration of field application, the modulation frequency, the types of bead that are used (e.g. depending on the size, susceptibility, magnetic anisotropy, shape, superparamagnetic, or ferromagnetic properties of the beads) and the concentration of beads. Concerning the field pattern, curved chains can be formed by applying fields with a curvature, for example. To form clusters of particles, a loop-shaped wire can for example be used. The particles will be attracted to the region of highest field in the centre of the wire loop. For obtaining loops or rings 8 of particles, a current wire 9 can be used with a segment that is freely accessible from all sides. This is illustrated in FIG. 25. The field lines will follow the edge of the current wire 9 and the particles will arrange to form a ring or loop 8. Particles having a long relaxation time or having hysteresis will remain in the loop-shape when the magnetic field is removed. Furthermore, magnetic particles initially ordered as chains can form loops or rings when the field is removed.

In the following description, the second aspect of the present invention will be further described by means of chains 10 of beads. This is only for the ease of explanation and is not limiting to the invention. In the following, the formation of chains 10 of particles will be discussed. The ratio λ of interaction energy of two parallel dipoles in contact and the thermal energy is given by:

$$\lambda = \frac{U}{kT} \Rightarrow U = \lambda kT \tag{2}$$

wherein U is energy of interaction between magnetic beads, k the Boltzmann-constant $1.38054 \; 10^{-23}$ J/K and T the temperature in Kelvin.

The energy of interaction U can also be described by:

$$U = \frac{\mu_0}{4\pi} \frac{m_1 m_2 - 3(m_1 \cdot \hat{r})(m_2 \cdot \hat{r})}{r^3} \tag{3}$$

wherein $\mu_0$ is the permeability of vacuum ($4\pi.10^{-7}$ H/m), $m_1$ and $m_2$ the magnetic moment of a first respectively a second magnetic particle or bead, r the center-to-center distance of the magnetic particles or beads and ρ is the unit vector in the direction of the path between two centres of particles. This can be broadened to particles with dissimilar radii. For example, in case of a mixture of large beads with large moments and small beads with small moments, the beads with larger moment will more strongly attract each other for a given center-to-center distance. As a consequence, the large particles can form chains while the particles having a smaller moment will collect around or as close as possible to the poles of the larger particles. Manipulating the larger particle chain directly manipulates the smaller particles. Combination of equations (2) and (3) with m1=m2 leads to:

$$\lambda = \frac{\mu_0}{4\pi} \frac{2m^2}{kTr^3} \quad (4)$$

wherein r is the centre-to-centre distance between the particles, and is equal therefore to the particle diameter if the particles are in close contact. In the case of 300 nm diameter magnetic beads obtainable from Ademtech, with a magnetic moment m of $1.5 \times 10^{-15}$ Am$^2$ in an excitation field of 0.1 T, $\lambda$ may have a value of about $4 \times 10^3$. Such a large ratio of interaction energy of two parallel dipoles in contact and the thermal energy implies that the force of magnetic interaction is much bigger than the thermal influence on the magnetic particles or beads, resulting in the formation of chains 10 of magnetic particles. When the ratio $\lambda$ decreases, the motional freedom of the beads in the chain 10 increases and the chains 10 show shape fluctuations. The chains 10 dissociate when the ratio becomes smaller than unity.

The force of interaction or attraction $F_{int}$ between magnetic particles or beads in attractive alignment (unlike when poles of the same nature are touching) can be represented by the following equation:

$$F_{int} = \frac{\mu_0}{4\pi} \frac{6|m_1||m_2|}{r^4} \quad (5)$$

wherein $F_{int}$ is expressed in N.

Preferably, according to the second aspect of the present invention, superparamagnetic particles or beads may be used. Superparamagnetic particles or beads are ferromagnetic beads so small that they quickly lose their magnetic moment in absence of an external magnetic field. Superparamagnetic particles or beads are readily magnetised to large magnetic moments, facilitating detection, yet the mutual magnetic attraction can be switched off, preventing irreversible aggregation. In general, superparamagnetic particles or beads with a diameter of, for example, about 300 nm may require a field of only 4 to 10 mT to form chains 10 of beads. The speed of chain formation and the chain length may be determined by the particle or bead concentration and the particle or bead magnetic moment [Zhang, Phys. Rev. E51, 2099 (1995)]. The chains 10 according to embodiments of the present invention may, for example, have a length in the order of about 100 particles.

The surface of the magnetic particles or beads may be prepared to allow reversible aggregation, i.e. the formation of multi-particle structures in the presence of a magnetic field and the dissociation of the multi-particle structures when the magnetic fields are subsequently removed. It is shown by experiments that reversible chain formation is possible with e.g. 300 nm particles obtainable from Ademtech. The surface of the beads may be prepared to avoid sticking and allow reversible chain formation. This may be done by, for example, applying a polymer layer for entropic repulsion, by steric hindrance and/or by applying electrical charges on the surface. At very high fields, some degree of irreversible binding may take place due to a too close approach and the resulting non-specific adhesion. In that case the applied fields should be reduced.

As already stated above, in a biosensor assay, the 'attract' and 'bind' phases need to be made as efficient and as fast as possible. In the 'attract' phase the beads are concentrated from the bulk of the fluid to a zone near the sensor binding surface. The time needed to attract the particles toward the binding surface should be as low as possible, lower than 30 minutes, preferably lower than 10 minutes, and more preferred lower than 1 minute.

In the 'bind' phase, the resulting bead ensemble is brought even closer to the binding surface in a way to optimise the occurrence of desired (bio)chemical binding to the capture or binding area on the sensor, i.e. the area where there is a high detection sensitivity by the sensors, e.g. magnetic sensors, and a high biological specificity of binding. It is not trivial to optimise the 'bind' process. Therefore, there is a need to increase the contact efficiency (to maximise the rate of specific biological binding when the bead is close to the binding surface) as well as the contact time (the total time that individual beads are in contact with the binding surface).

Contact efficiency and contact time have been discussed above with respect to the first aspect of the present invention.

With regard to contact time, when a large number of beads or particles is attracted to the binding surface of a sensor device and the complete binding surface becomes covered with magnetic particles, the multi-particle structure will be very dense but also static and rigid. Due to translational constraints, a large fraction of particles cannot reach the binding surface and will not have a chance to form a desired specific biochemical bond. This causes a loss of signal in the biosensor and thus a false reading or an unnecessarily long assay time.

The above analysis leads to the conclusion that multi-bead structures do generate a high contact area with the binding surface, but cannot be beneficially used in a magnetic biosensor due to the low translational dynamics inside the multi-bead structure. However, the inventors have realised that there is a way to solve this. Therefore, it must be realised that inside the multi-bead structures, individual beads maintain a freedom of rotation. For example, superparamagnetic beads have a very weak magnetic anisotropy, so a very weak coupling exists between the magnetic moment and the physical orientation of the particle. Thermal energy causes rotation of the magnetic beads (rotational diffusion) and as a result the beads will expose a significant part of their surface area to the binding surface. The surface-to-surface exposure will allow the formation of specific biochemical bonds.

In other words, multi-bead structures can be used in a biosensor provided that, according to the present invention, the structures are regularly or irregularly randomised, e.g. by removing and re-applying the magnetic fields attracting the multi-particle structures to the binding surface of the sensor device, or by rotational excitation of the beads and bead structures, or by the application of fluid motion such as stirring or acoustic vibrations, With randomised is meant that magnetic particles which are attracted to the binding surface but which do not bind to the binding surface are shortly moved away from the binding surface but never get very far from the binding surface, i.e. they stay within a short distance from the binding surface in the z-direction. Preferably, they stay within 100 µm from the binding surface and more preferably they stay within 10 µm from the binding surface in a direction substantially perpendicular to the binding surface. According to the invention, the particles are moved away from the binding surface such that 90% of the magnetic particles which are part of a multi-particle structure stay within 10% or less of the sample volume. Particles do not disperse back into the complete sample volume. The repeated attractions and randomisations ensure that biological material coupled to magnetic beads have a high probability to be at least once in contact with the binding sites on the binding surface of the sensor device during the total assay, i.e. that all targets have a substantial probability to have a contact time with binding sites on the binding surface of the sensor device.

The magnetic particles or beads are thus attracted toward and onto the binding surface by means of a magnetic field gradient. The beads involved in the binding process will be part of multi-bead structures, characterised in that the beads have a probability larger than 80% to have the surface of at least one other bead in their vicinity, i.e. within a bead-surface to bead-surface distance of two times the bead diameter.

In conclusion, the assay should be designed to achieve maximum specific binding (by attraction of the beads toward the binding surface) and minimum hindering of binding (all beads should have a significant probability to interact with binding sites on the binding surface of the sensor device), and minimum unwanted unbinding (due to forces breaking the desired bonds between beads and binding surface).

As explained, rotation of magnetic particles and multi-bead structures may be used to optimise the exposure rate and binding rate in a biochemical assay. The rotation can be caused by thermal energy but can also be generated or enhanced by time-varying applied fields. Firstly, when magnetic particles are present in solution, rotation of these magnetic particles can enhance the interaction and binding rate between the biological material in solution and the surface of the magnetic particles. This, for example, applies to the fishing or catching phase in an assay, wherein magnetic particles are used to bind to specific biological material in a sample solution and/or to extract this material. Secondly, when magnetic particles are rotated with respect to another body, for example the surface of a biochip or the surface of a cell, the interaction and binding rate between the label and the other body can be enhanced. The increase of the binding rate may particularly be of importance when the surface area of the label is large with respect to the size of the relevant molecular binding region on the magnetic particle. This is, for example, the case in low-concentration assays, when a catching or fishing step yields magnetic particles with only very little biological material of interest on the magnetic particle surface. For reference, some calculations on the role of orientation and rotation in biomolecular kinetics can be found in "K. S. Schmitz and J. M. Schurr: 'The role of orientation constraints and rotation diffusion in biomolecular solution kinetics', J. Phys. Chem., vol. 76, p. 534 (1972)".

The ideal rotation speed is given by an optimal binding rate at acceptable unbinding rate for the biochemical bond that needs to be formed in the given assay time. In other words, the rotation is optimised for sensitivity as well as specificity. To avoid removal of the desired specific bindings, the applied forces need to be below 1 nN.

Figure 3:
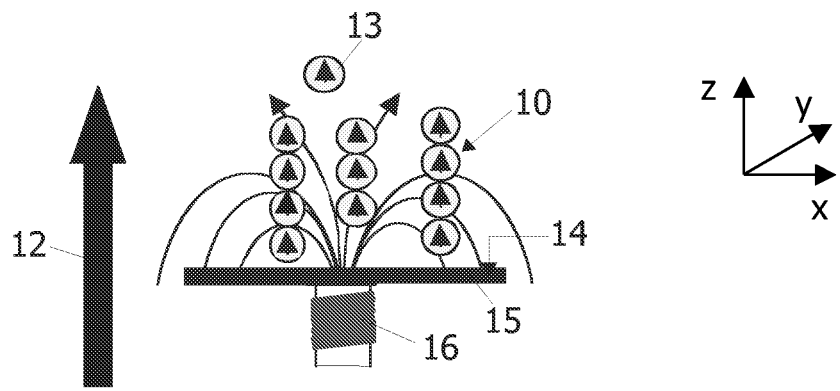
FIG. 3 illustrates magnetic bead columns formed by magnetising beads in a uniform magnetic field.

According to a first embodiment of the second aspect of the present invention, the use of magnetic fields which are oriented essentially perpendicularly to the sensor surface 14 of the sensor device 15, i.e. according to the orientation axes mentioned in the drawings, oriented in the z-direction, is described. This is illustrated in FIG. 3. A uniform magnetic field, indicated by arrow 12, induces the formation of particle or bead chains 10, comprising a plurality of magnetic particles or beads 13, as described earlier. Then, a magnetic field gradient may be generated for attracting the magnetic particle or bead chains 10 toward the surface 14 of the sensor device 15. The magnetic field gradient may be provided by at least one magnetic field gradient generating means 16. In the example illustrated in FIG. 3 the magnetic field gradient is generated by means of an external coil 16 which is positioned under the sensor device 15 and which is used to generate forces toward and from the sensor surface 14. In embodiments of the present invention, the sensor device 15, which may be used according to the present invention, may comprise at least one magnetic sensor element and at least one magnetic field generating means for generating a magnetic field for forming bead chains 10. The magnetic sensor element may preferably be a magneto-resistive sensor element such as, for example, a GMR, TMR or AMR sensor element. Bio-molecular diagnostics generally involves a re-usable reader system and a disposable unit in which the sample is entered. Field-generating coils can be part of the reader or of the disposable unit. In the disposable unit, the coil, can be embedded in the outer material (generally plastic) or be integrated onto a chip that also performs the detection of the magnetic field of the beads. According to alternative embodiments, the sensor device 15 may comprise at least one non-magnetic sensor element, e.g. an optical sensor element.

Figure 26:
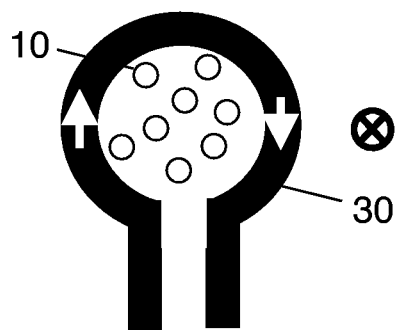
FIG. 26 is a view along the z-axis, i.e. along the long axis of the bead chains according to an embodiment of the invention.

The z-oriented chains of beads can easily be concentrated into a small area close to or even onto the sensor by applying a small magnetic gradient field in addition to a more uniform field with larger magnitude. This is sketched in FIG. 26 which shows a view along the z-axis, i.e. along the long axis of the bead chains 10 which are represented as open circles.

Figure 27:
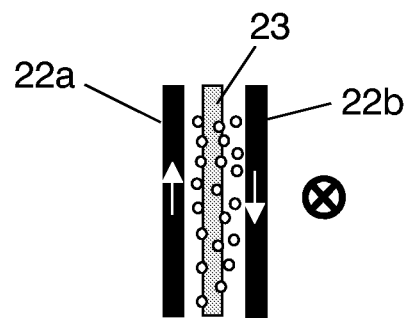
FIG. 27 is a top view along the long axis of the bead chains of a configuration comprising two current wires with a magnetic sensor element in the middle.

The z-oriented field generates the bead chains 10. The local current wire generates a field gradient in the middle of the loop 30. When the field generated by the loop 30 has the same orientation as the external field, the field is larger inside the loop 30 than outside the loop. Therefore, the chains 10 are attracted into the middle of the loop 30. When the current is reversed, the field generated by the loop 30 will oppose the external field in the middle of the loop 30, and as a consequence the chains 10 will be pushed out of the loop 30. Similarly, FIG. 27, which is a top view along the long axis of the bead chains 10 of a configuration comprising two current wires with a sensor in the middle, illustrates how currents in current wires can be used to concentrate bead chains 10 onto a sensor binding region.

Figure 4:
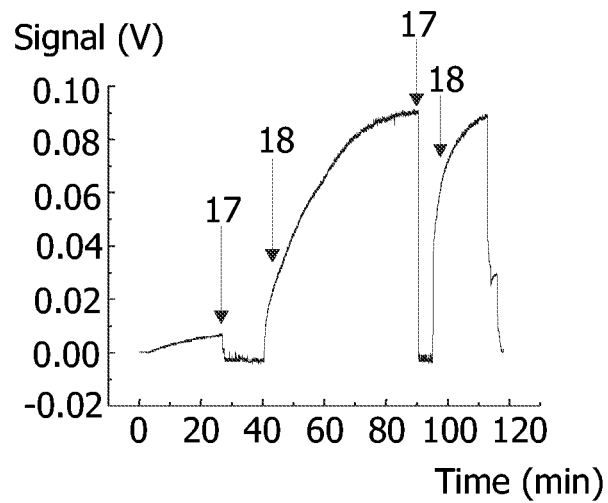
FIG. 4 illustrates the effect of repelling and attracting magnetic bead columns to the surface of a magnetic sensor according to an embodiment of the present invention.

It has to be noted that the presence of a magnetic sensor or other magnetic materials in a chip can influence the fields near the sensor, due to magnetostatic or flux guiding properties. An advantage of the out-of-plane chain orientation is that flux guiding is low due to the in-plane shape anisotropy of magnetic thin films. The magnetic field gradient may be modulated in-phase with the modulation of the chain-forming magnetic field 12, which results in attraction of bead chains 10 to the sensor surface 14. When the modulation is applied in anti-phase, the field gradient is reversed and as a result the bead chains 10 may be repelled from the sensor surface 14. This is illustrated in FIG. 4 which shows the effect of repelling (reference number 17) and attracting (reference number 18) magnetic particle or bead chains 10 from and to the surface 14 of a sensor device 15 respectively. Repelling the bead chains 10 may generate stringency, which may differentiate between (strongly) bound and weakly bound beads or particles 13 on the sensor surface 14.

The flow resistance of bead chains 10 is lower for chains 10 travelling along their length axis than for chains 10 travelling perpendicular to their long axis. In this way the shape of the container of the fluid sample and the resulting required travelling direction toward the sensor can influence the choice of applied fields.

In the above, both the magnetic field for forming the multi-particle magnetic structures, in the example given chains 10, is applied in a direction substantially perpendicular to the sensor surface 14, i.e. in the z-direction. Due to these fields perpendicularly applied to the sensor surface 14, the particle or bead chains 10 are oriented in a direction substantially perpendicular to the sensor surface 14, as is illustrated in FIG. 3.

Figure 28:
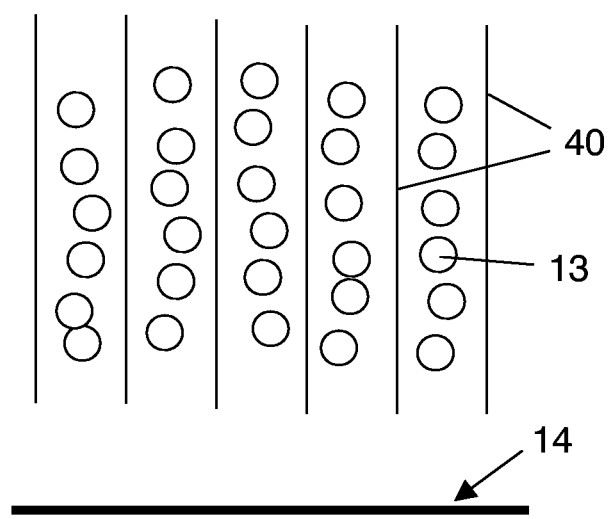
FIG. 28 illustrates a sensor device with as binding surface a porous multi-channel structure.

In case the binding surface 40 is parallel to the sensor surface 14, located on or near the sensor surface 14, the above-described embodiment has the disadvantage that not all magnetic particles 13 can come very close to the binding surface 40 due to the multi-particle structures 10 having their long axis in a plane perpendicular to the plane of the binding surface 40. However, in case the binding surface 40 is a porous medium with walls essentially perpendicular to the sensor surface 14, the beads 13 in the multi-particle structure 10 which are lying in a plane substantially parallel to the binding surface 40 can make good contact to the binding surface 40. This is illustrated in FIG. 28, where the binding surface 40 is provided on walls of a porous multi-channel structure, which walls are oriented perpendicularly with respect to the sensor surface 40. The channels in the multi-channel structure may e.g. be tubes or slits. The multi-particle structures 10 may attracted to the binding surface 40 e.g. by means of a magnetic gradient in a direction perpendicular to the binding surface 40, in the embodiment shown parallel to the sensor surface 14. After the 'attract' phase, a 'binding' phase takes place, i.e. binding sites on particles 13 in the multi-particle structures 10 come into contact and bind with binding sites on the binding surface 40. According to the present invention, the position of individual magnetic particles 13 in the multi-particle structures 10 is randomised with respect to the binding sites on the binding surface 40 to give the binding sites on the individual particles 13 in the multi-particle structures 10 a substantial probability to have a contact time with binding sites on the binding surface 40. This randomisation may be done by changing the magnetic field gradient in a direction perpendicular to the binding surface 40. After the binding phase, the multi-particle structures 10 are no longer attracted to the binding surface 40, unbound particles 13 are washed away and detection of particles bound onto binding surface 40 can take place. This detection can e.g. be a magnetic detection or an optical detection. Typically in biological tests the concentration of beads is limited so that a plurality of bound beads in one channel are often not to be expected, and thus the presence of a bead in a microchannel can be optically detected. If the concentration is expected to be higher, a measurement period can be split up into a plurality of time intervals. A high target concentration will be detected very rapidly (for example after one time interval, e.g. in a few seconds) while low target concentrations can be detected after a much longer processing time (after a plurality of time intervals, e.g. minutes to hours). Alternatively, if a plurality of beads present in one microchannel are to be optically detected, the labels can be made fluorescent. If light is impinged into the microchannels, all beads will receive light, and fluorescent light will be sent out, so that the presence of all the beads in the microchannel can be detected.

When the binding surface 40 is essentially parallel to the sensor surface 14, in particular the binding surface 40 is part of the sensor surface 14, to achieve a small distance between most of the particles or beads 13 in a chain 10 and the binding surface 40, it is advantageous to align the bead chains 10 along the binding surface 40, i.e. to apply magnetic fields with strong in-plane components, i.e. in the x- or y-direction. This is described in a second embodiment of the present invention. Magnetic fields with strong in-plane components may be applied by off-chip as well as by on-chip field-generating means. On-chip field generation has the strong advantage that the unavoidable magnetic crosstalk to the magnetic sensing element, e.g. a GMR, is well defined.

Hence, according to the second aspect of the present invention, a magnetic field generating means is adapted to form multi-particle magnetic structures 10 which have a long axis lying parallel to the binding surface 40.

A magnetic field is applied with a strong in-plane component parallel with the binding surface 40 of the sensor device 15, e.g. by placing the device near a permanent magnet and/or a coil. Multi-particle magnetic structures, in the example given chains 10, are formed and attracted toward the binding surface 40. According to this second embodiment, preferably, at least one current wire 19 may be positioned close to and underneath the binding surface 40 of a sensor device 15, preferably within 1 mm, more preferably within 30 micrometer and most preferred within 3 micrometer. The formed particle or bead chains 10 then orient substantially parallel to the surface 14 of the sensor device, in a direction substantially perpendicular to the direction of the current in the at least one current wire 19, and will be pulled toward the binding surface 40, as is sketched in FIG. 5. In this figure, the current direction in the current wire 19 is indicated by arrow 20 and the orientation of the particle or bead chains 10 is indicated by arrow 21.

It has to be noted that it may be advantageous to first concentrate beads 13 near the sensor by using fields essentially perpendicular to the sensor surface 14, and then switch to essentially in-plane fields to enhance the contact efficiency between the multi-particle structures 10 and the binding surface 40. This process can be repeated several times in order to combine (i) efficient concentration of beads or particles 13 near the binding surface 40, (ii) efficient contact between beads 13 and binding surface 40, and (iii) regular re-arrangement and randomisation of the beads 13 in order to give all beads 13 a substantial probability to interact with the binding sites on the binding surface 40. Changing between attracting the particles to the binding surface 40 and randomising may be controlled by means of a reader, or it may be implemented on a chip which may be part of the sensor device 15 or which may be a separate signal-processing chip in the sensor device 15.

Local current wires are useful to make field gradients (unit T/m) with relatively small currents, e.g. smaller than 100 mA. It is advantageous to use small fields in order to minimise the fields and particularly the in-plane fields applied to the sensor, in particular in case it is a magnetic sensor. The application of high fields can change the sensitivity of the sensor, in particular the sensitivity of a magnetic sensor, and cause changes of its magnetic structure, e.g. domain wall changes, magnetic loops, hysteresis.

Furthermore it may be advantageous to generate said fields on the sensor chip so that said fields are well defined which avoid tight mechanical tolerances in the cartridge and read-out station.

Figure 5:
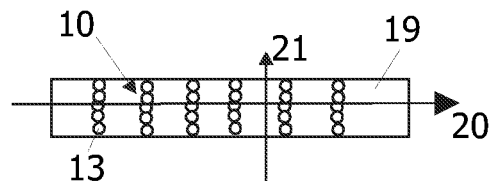
FIG. 5 is a top view of a current wire according to an embodiment of the present invention.

In the absence of other field-generating means a current wire 19 with rectangular cross-section, as is the case in the example given in FIG. 5, may generate the highest fields and highest field gradients at its edges. This means that particles or beads 13 near the edges of the current wire 19 will be more strongly attracted than particles or beads 13 in the middle of the current wire 19 (see further).

Figure 6:
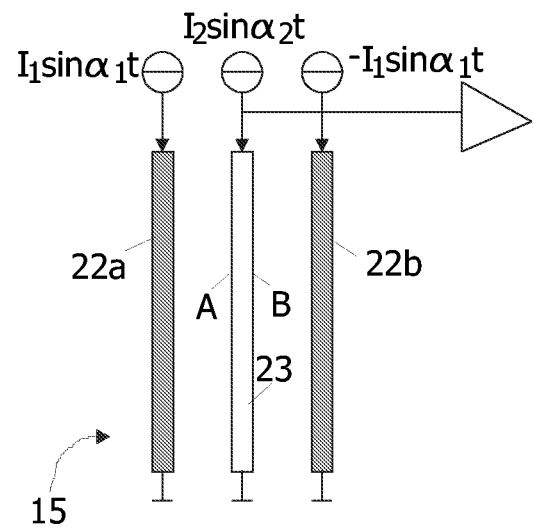
FIG. 6 is an illustration of a sensor configuration according to an embodiment of the invention for attracting beads to the binding surface of a sensor device.
Figure 7:
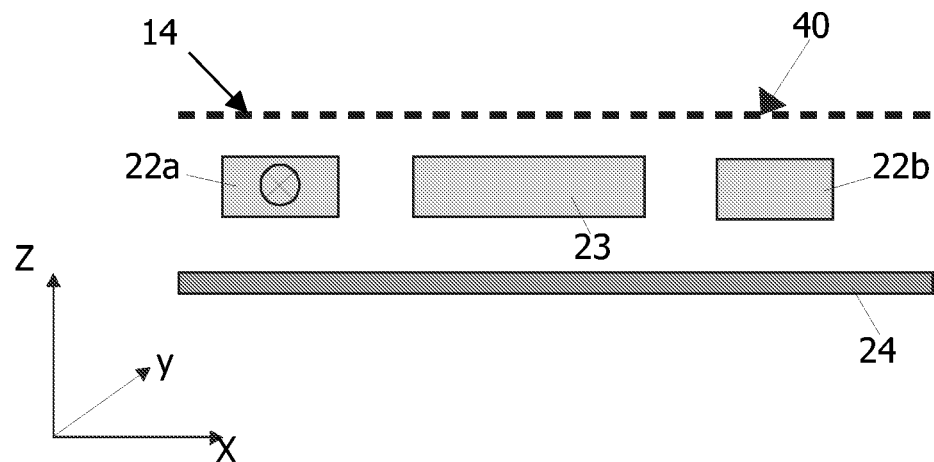
FIG. 7 is a cross-section of the sensor configuration of FIG. 6.

In a further embodiment of the second aspect of the present invention, the sensor device 15 may comprise as magnetic field gradient generating means at least two current wires 22a, 22b and at least one magnetic sensor element 23, wherein at least a first current wire 22a is positioned at a first side A of the magnetic sensor element 23 and at least a second current wire 22b is positioned at a second side B of the magnetic sensor element 23, as is illustrated in FIGS. 6 and 7, where an example of a possible sensor configuration according to this embodiment of the invention is illustrated. According to embodiments of the invention, the at least one magnetic sensor element 23 may preferably be a magneto-resistive sensor element such as for example a GMR, TMR or AMR sensor element.

According to this embodiment of the invention, first a magnetic field or combination of magnetic fields is applied, which induces the formation of multi-particle magnetic structures or magnetic bead chains 10, comprising a plurality of magnetic particles or beads 13, as described earlier, and having a long axis substantially parallel with the binding surface 40 of the sensor device 15. A strong magnetic force may then be generated along the z-axis near the binding surface 40, in the sensitive area of the sensor element 23, e.g. by applying currents in at least one current wire. One example is to use a field oriented essentially along the z-axis (out-of-plane orientation) and to apply currents in opposite directions in the current wires 22a, 22b. Thus attracted (in case the fields are generated to have the highest magnitude above the sensor) multi-particle magnetic structures or magnetic bead chains 10 may then be detected by at least one magnetic sensor element by applying currents in the at least two current wires 22a, 22b in the same direction, in that way effectively measuring the amount of beads or particles 13 present on the binding surface 40. Alternatively, the multi-particle structures may be detected by e.g. an optical detection element.

Also, fields oriented essentially along the x- or y-axis may be used according to the present invention, i.e. for in-plane orientation of the magnetic multi-particle structures. A magnetic force may be generated along the z-axis by applying currents in at least one current wire 22. The force will be attractive when the fields from the current wire 22 increase the local field above the surface, thus generating a positive field gradient toward the sensor surface 14. A disadvantage of applying in-plane fields is that these are along the sensitive direction of the magnetic sensor and will influence the properties of a magnetic sensor device 15. One solution is to time-separate the two processes: sequentially actuate and detect the particles.

FIG. 6 shows a possible configuration of a magnetic sensor device 15 for integrated attraction and detection of magnetic beads or particles 13 oriented in multi-particle magnetic structures. The magnetic sensor device 15 in this example may comprise a magnetic sensor element 23 and at least a first and second current wire 22a resp. 22b. This may be a preferred sensor configuration for attracting magnetic beads or particles 13 in multi-particle magnetic structures 10 close to the binding surface 40. A same current but in opposite directions is applied to the first and second wires 22a, 22b positioned at both sides A, B of the magnetic sensor element 23. The benefit of this will be described hereinafter. For the ease of explanation, the following discussion will be done by means of a single bead 13 and with fields generated only by local on-chip wires. It is, however, to be understood that this may also be applied to the multi-particle magnetic structures 10 of the present invention and can be generalized when more field-generating means are added.

Generally speaking the magnetic force on a single bead 13 is given by:

$$F_{magn} = -\nabla u = -\nabla(\vec{m} \cdot \vec{B}) \qquad (9)$$

wherein $F_{magn}$ is the magnetic force applied to the magnetic bead 13 for attracting it toward the binding surface 40, u the potential energy associated with the magnetic moment m of the bead or particle 13 and B the applied magnetic field.

In case of an integrated excitation sensor device 15, i.e. where the magnetic field gradient generating means is incorporated in the sensor device 15, as is the case in this embodiment, and where the magnetic beads or particles 13 are superparamagnetic, the magnetic force on a single bead 13 reduces to:

$$F_{magn} = -\mu_0 \chi_{bead} \nabla (\vec{H})^2 \qquad (10)$$

wherein $\chi_{bead}$ is the magnetic susceptibility of the bead and H the magnetic field strength. For example, for 300 nm beads obtainable from Ademtech, $\chi_{bead}$ equals 4.22 $10^{-20}$.

The attraction force of equation (10) may be split up in x and z components, i.e. in a horizontal resp. vertical component:

$$F_{magn,x} = -\mu_0 \chi_{bead} \frac{\partial (H_x)^2}{\partial x} \qquad (11)$$

and $$F_{magn,z} = -\mu_0 \chi_{bead} \frac{\partial (H_z)^2}{\partial z} \qquad (12)$$

FIG. 7 shows a cross-section of the sensor device 15 of FIG. 6. A magnetic sensor element 23 and a first and second current wire 22a, 22b are positioned on top of a substrate 24. The dashed line, indicated by reference number 14, represents the sensor surface of the sensor device. A portion of the sensor surface 14 is the binding surface 40 comprising binding sites (not represented in detail). A co-ordinate system has been introduced in FIG. 7 in order to make the following explanation more clear.

Figure 8:
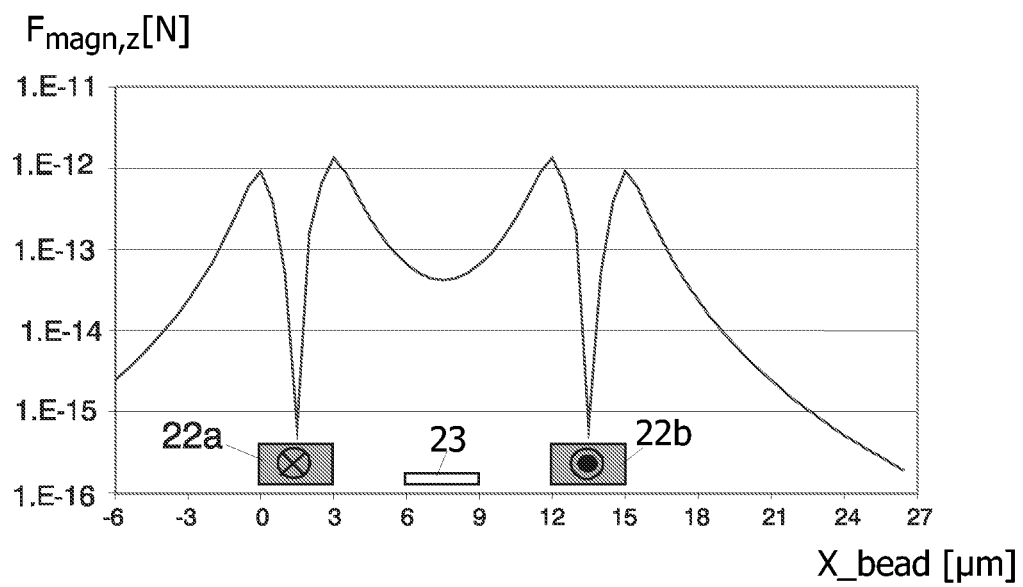
FIG. 8 shows the vertical magnetic force at a distance $z=0.64$ µm from the binding surface, as a function of the position of the beads for the sensor configuration of FIGS. 6 and 7.

FIG. 8 shows the vertical magnetic force $F_{magn,z}(x)$ (see equation (12)), i.e. the magnetic force in the direction perpendicular to the sensor surface 14, the z-direction as indicated by the co-ordinate system in FIG. 7, as a function of the position of the magnetic particle or bead 13 in the sensitive direction of the sensor, the x-direction. For the construction of FIG. 8, $F_{magn,z}(x)$ is determined at a distance of 0.64 μm from the binding surface 40 (i.e. z=0.64 μm). For the present situation, the excitation currents in the first and second current wire 22a, 22b flow in opposite directions as explained above with respect to FIG. 6 and as indicated in FIG. 8 by ⊗ and ⊙. Furthermore, the graph in FIG. 8 is valid for excitation currents $I_{w1} = -I_{w2} = 50$ mA and for 300 nm magnetic particles obtainable from Ademtech. Hereby is $I_{w1}$ the current through the first current wire 22a and $I_{w2}$ the current through the second current wire 22b. It can be seen from FIG. 8 that the vertical magnetic force $F_{magn,z}(x)$ is much smaller at positions in the middle of the current wires 22a, 22b than at the edges of the current wires 22a, 22b. Magnetic particles or beads 13 will thus feel a bigger force in the z-direction when they are close to the edges of the current wires 22a, 22b than when they are close to the centre of the current wires 22a, 22b. Hence, magnetic particles 13 will be attracted more closely toward the edges of the current wires 22a, 22b than toward the centre or middle of the current wires 22a, 22b (see further).

Figure 9:
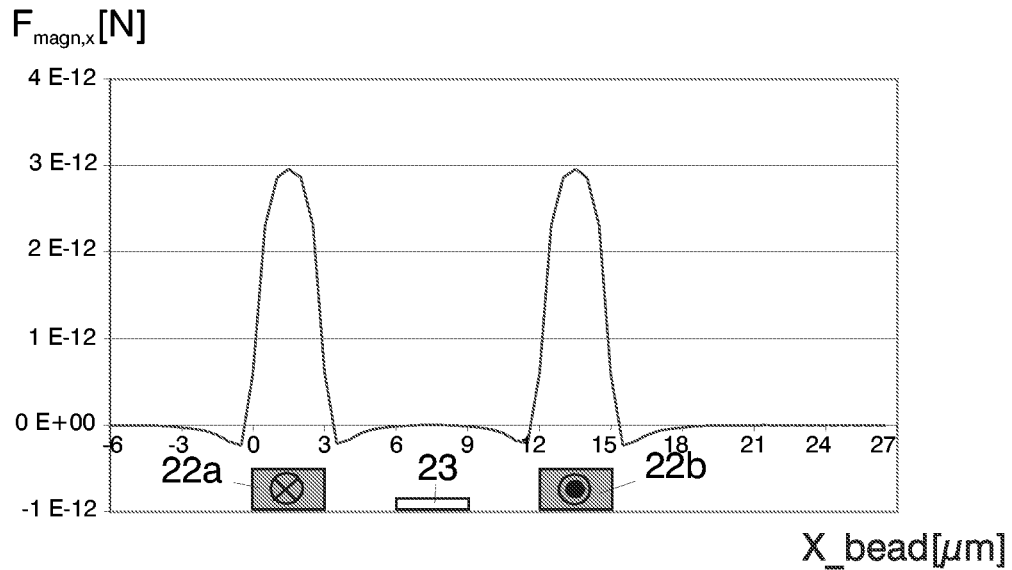
FIG. 9 shows the horizontal magnetic force at a distance $z=0.64$ µm from the binding surface, as a function of the position of the beads for the sensor configuration of FIGS. 6 and 7.

FIG. 9 shows the corresponding horizontal magnetic force $F_{magn,x}(x)$ (equation (11)), i.e. the magnetic force in the sensitive direction of the magnetic sensor device 15, the x-direction as illustrated in FIG. 7 by the co-ordinate system, and this as a function of the position of the magnetic beads 13 in the x-direction. Again, for the construction of FIG. 9, $F_{magn,x}(x)$ is determined at a distance of 0.64 μm from the binding surface 40 (i.e. z=0.64 μm). It can be seen from FIG. 9 that the horizontal magnetic force $F_{magn,x}(x)$ is much bigger in the middle of the first and second current wires 22a resp. 22b than it is at the edges of the current wires 22a, 22b. This means that magnetic particles or beads 13 located above the centre of the current wires 22a, 22b will be more transported in the x-direction than magnetic particles or beads 13 located above the edges of the current wires 22a, 22b. The same happens to the formed multi-particle magnetic structures 10. Forces acting on a multi-particle magnetic structure 10 are larger than forces acting on a single bead 13 (if the multi-particle magnetic structure 10 e.g. comprises a plurality of beads 13 of the same type as the one compared to), due to the larger magnetic moments of a multi-particle magnetic structure 10.

Figure 10:
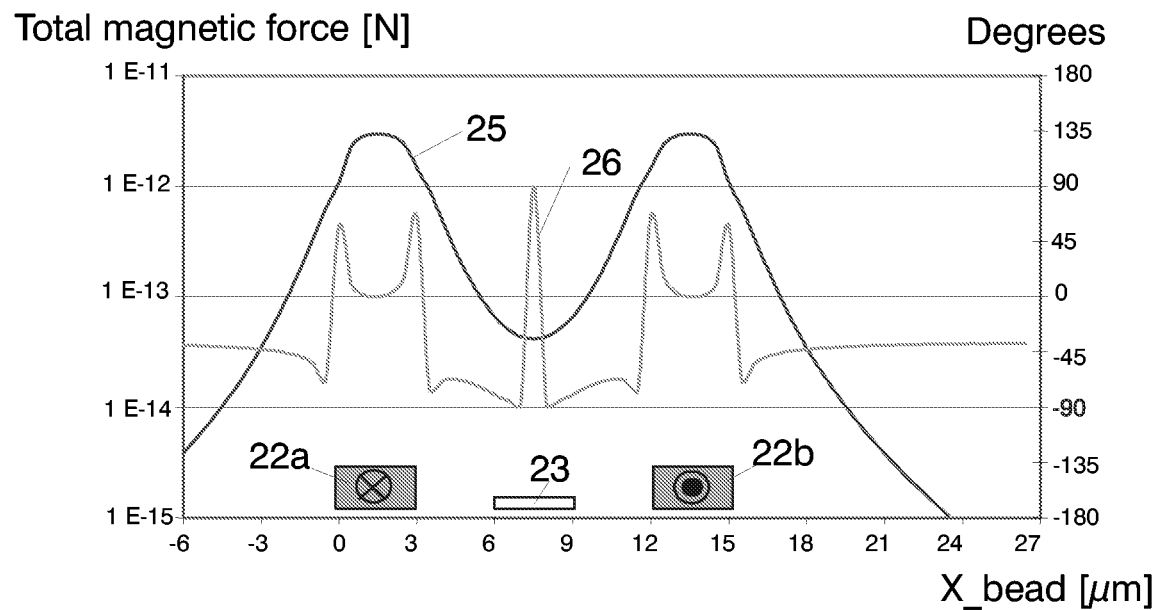
FIG. 10 shows the magnitude and phase of the magnetic force at a distance $z=0.64$ µm from the binding surface, as a function of the position of the beads for the sensor configuration of FIGS. 6 and 7.

FIG. 10 shows the magnitude, indicated by curve 25, and phase, indicated by curve 26, of the resulting magnetic force (combination of $F_{magn,z}(x)$ of FIG. 8 and $F_{magn,x}(x)$ of FIG. 9). From FIG. 10 it is clear that above the centre of the current wires 22a, 22b the magnetic field is perfect in-plane oriented (0°). The curves depicted in FIG. 8, FIG. 9 and FIG. 10 are obtained under the condition that no multiple-particle structures are formed and that no external magnetic field is applied.

Because of the above-described forces, the magnetic particles or beads 13 are transported over the sensor surface 14 towards the edges of the first and second current wire 22a, 22b.

The particles or beads 13 are also affected by gravitational force. The gravitational force on the magnetic particles or beads 13, $F_{grav}$, equals:

$$F_{grav} = \frac{4}{3}\pi \cdot r^3 \cdot \Delta\rho \cdot g = 1.5 \cdot 10^{-15} [N] \quad (13)$$

wherein r is the radius of the magnetic particle or bead 13, $\Delta\rho$ the mass density difference between the bead and the fluid and g is the acceleration due to gravity (9.81 N/kg). As a result, the distance of approach ξ at the surface 14 of the sensor device 15, also called sometimes distance of attraction, and also referred to as the local barometric height distribution, equals:

$$\xi = \frac{kT}{F_{magn.z} + F_{grav}} \quad (14)$$

Figure 11:
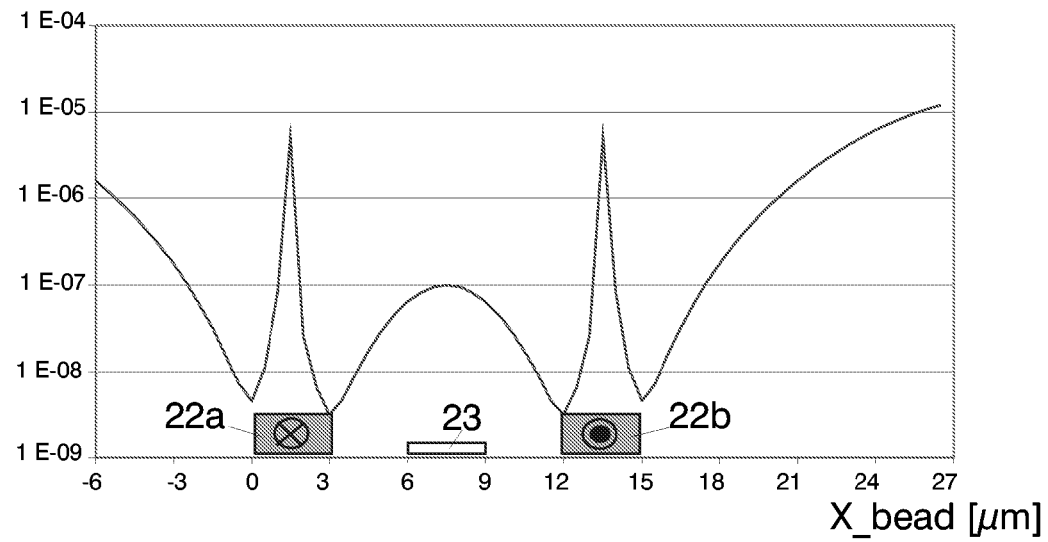
FIG. 11 illustrates the local barometric height at a distance $z=0.64$ µm from the binding surface, for beads in the neighbourhood of the sensor configuration of FIGS. 6 and 7.
Figure 12:
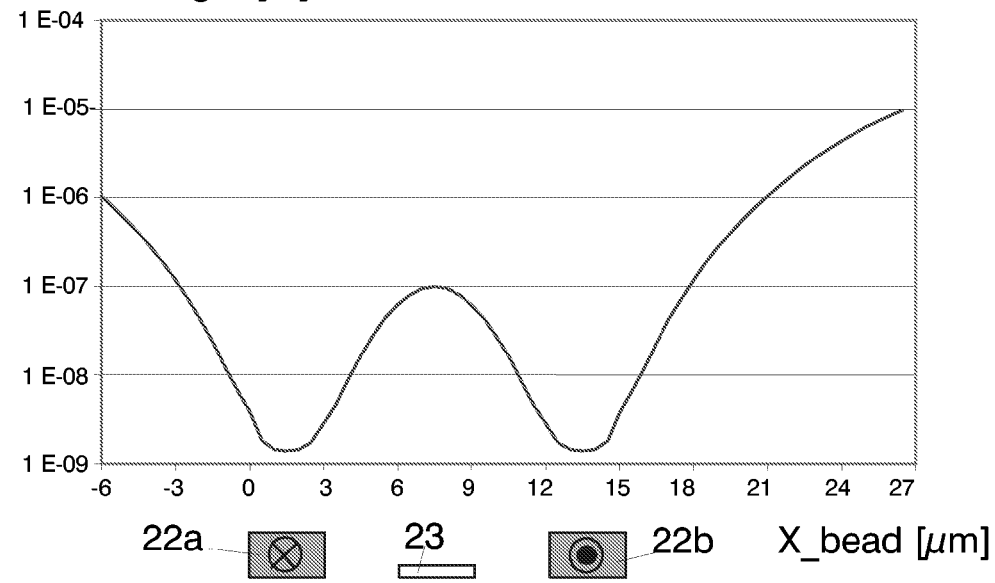
FIG. 12 illustrates the local barometric length at a distance $z=0.64$ µm from the binding surface, for beads in the neighbourhood of the sensor configuration of FIGS. 6 and 7.

The distance of approach or the barometric height distribution ξ is illustrated in FIG. 11, which illustrates the barometric height due to the vertical magnetic force $F_{magn,z}(x)$ plus gravitation. This curve is obtained under the condition that no multi-particle structures are formed and that no external magnetic field is applied. From this figure it can be concluded that, for the configuration with the dimensions described in FIGS. 6 to 12, in the range −3 μm≤x≤18 μm, which is one wire-width added to both sides of a sensor-wire structure, except at positions in the middle of the first and second current wire 22a, 22b, the local barometric height or distance of approach ξ≤100 nm. As a result, the magnetic particles or beads 13 are attracted very close to the binding surface 40, which facilitates efficient bio-chemical binding. FIG. 12 illustrates the local barometric length in the direction of the total force, i.e. the barometric length due to magnetic force plus gravitation. The difference between FIG. 11 and FIG. 12 is that in FIG. 11 vertical magnetic forces, the gravity and a bead distribution in the z-direction are dealt with, therefore called the barometric height, while FIG. 12 is dealing with a distribution of beads in the direction of the force, which is not perpendicular to the sensor. Therefore, this is called barometric length.

Figure 13:
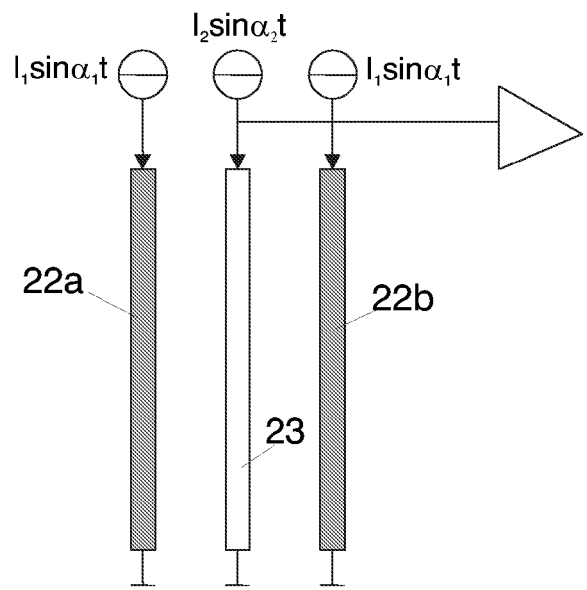
FIG. 13 is an illustration of a sensor configuration for detecting beads according to an embodiment of the present invention.
Figure 17:
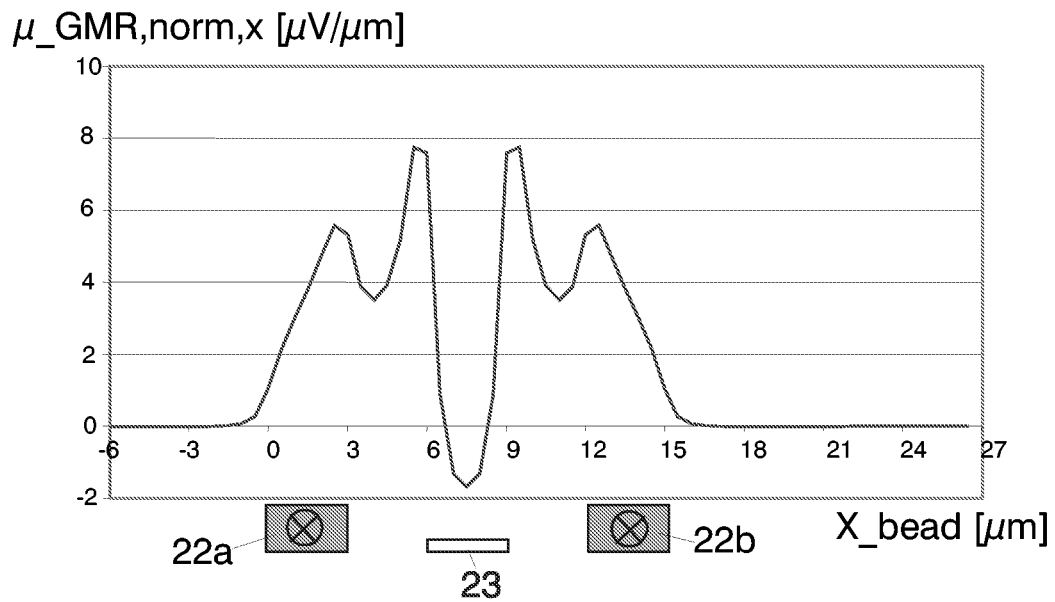
FIG. 17 illustrates the common mode sensitivity at a distance $z=0.64$ µm from the binding surface, for the sensor configuration of FIG. 13.

The above-obtained range (−3 μm≤x≤18 μm), which is one wire-width added to both sides of the sensor-wire structure, fits well on the common-mode response curve of the sensor device 15, depicted in FIG. 17, which is obtained when in the first and second wire 22a, 22b currents of an equal amplitude flowing in a same direction are applied, as is illustrated in FIG. 13. The common mode curve is the detection sensitivity of the sensor as a function of the position of the beads on the sensor surface under the condition that the currents in both current wires are flowing in the same (therefore common mode) direction. This configuration allows for the detection of magnetic particles or beads 13.

Figure 14:
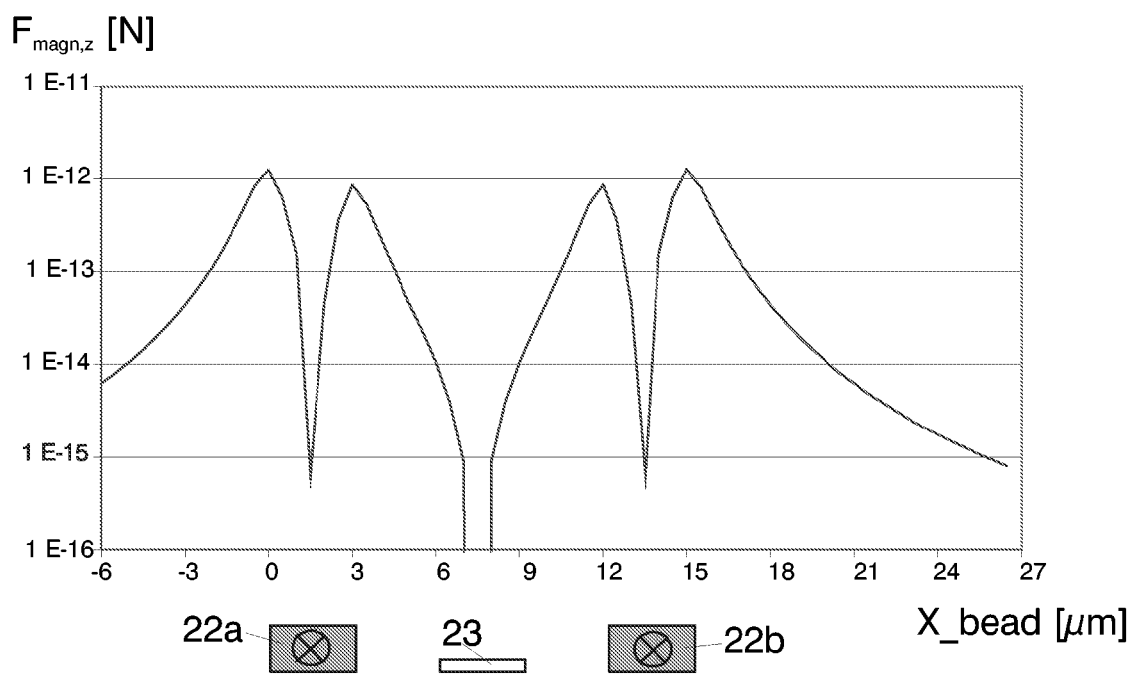
FIG. 14 shows the vertical magnetic force at a distance $z=0.64$ µm from the binding surface, as a function of the position of the beads for the sensor configuration of FIG. 13.
Figure 15:
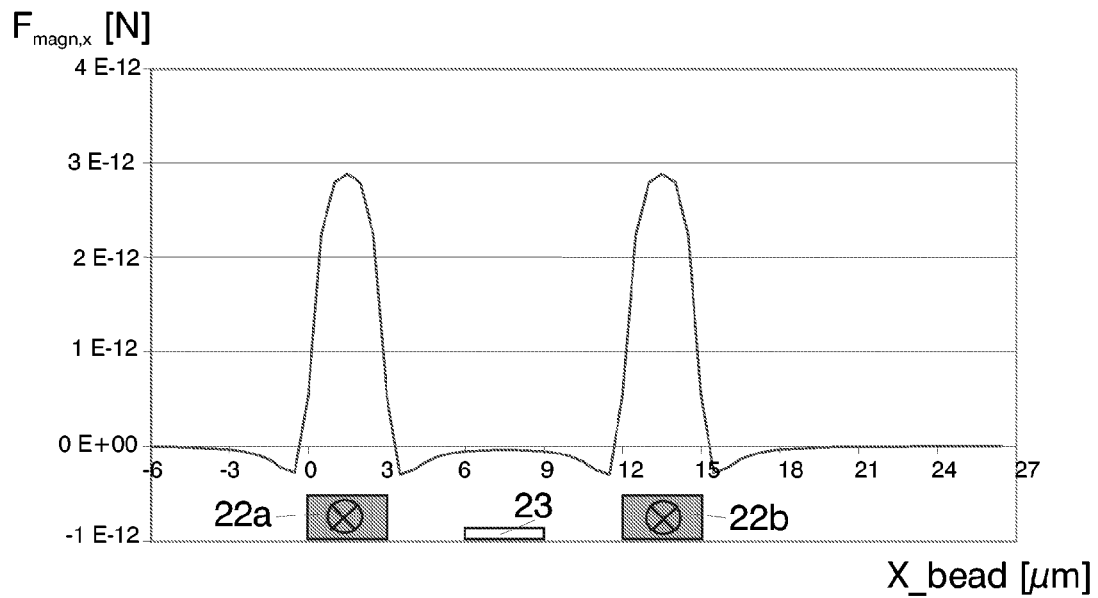
FIG. 15 shows the horizontal magnetic force at a distance $z=0.64$ µm from the binding surface, as a function of the position of the beads for the sensor configuration of FIG. 13.
Figure 16:
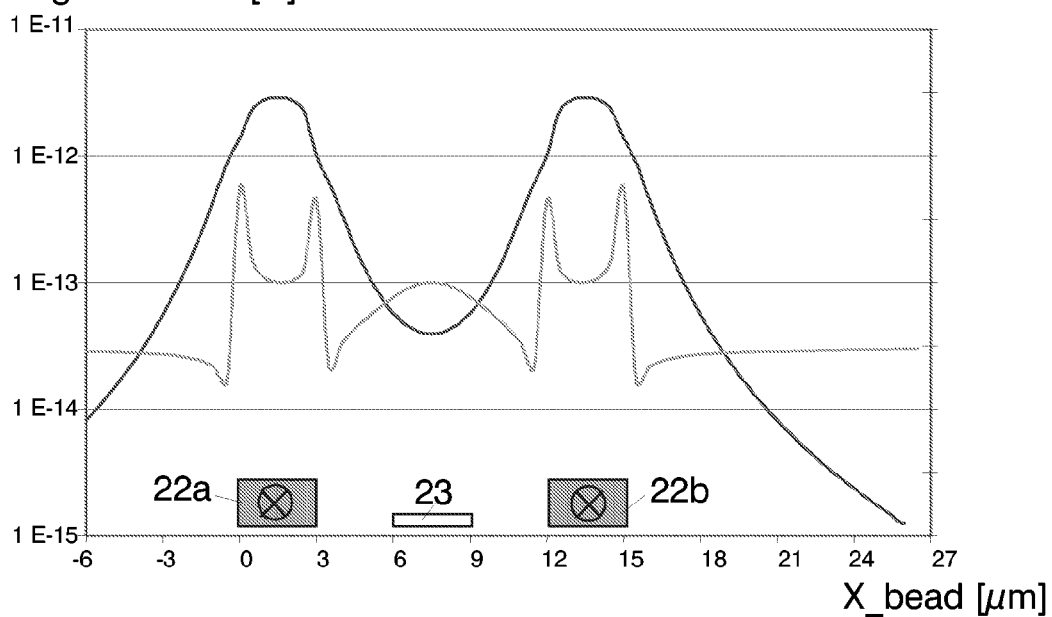
FIG. 16 shows the magnitude and phase of the magnetic force at a distance $z=0.64$ µm from the binding surface, as a function of the position of the beads for the sensor configuration of FIG. 13.
Figure 18:
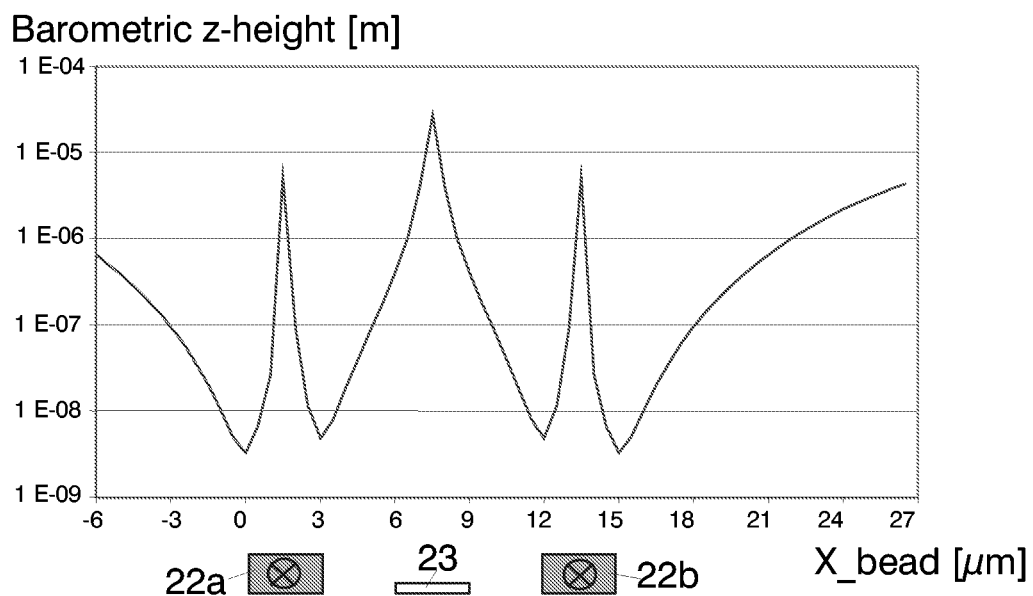
FIG. 18 illustrates the local barometric height at a distance $z=0.64$ µm from the binding surface, for beads in the neighbourhood of the sensor configuration of FIG. 13.

In FIG. 14, FIG. 15 and FIG. 16 resp. the vertical magnetic force, the horizontal magnetic force and the total magnetic force are illustrated for the case where equal currents flow in the same direction through the first and second current wire 22a, 22b. FIG. 17 illustrates the common mode response curve in the yz plane for the sensor configuration in FIG. 13. In FIG. 18 the barometric height or distance of approach of the magnetic particles or beads 13 in the case of currents with same amplitude applied in the same direction in both the first and second current wire 22a, 22b. The curve in FIG. 18 shows that the magnetic particles or beads 13 are far less attracted to the binding surface 40, so that binding is not optimal.

This embodiment of the invention has the advantage that both means for attraction of beads 13 and means for detection of beads 13 are integrated on the magnetic sensor substrate 24. In this embodiment, no external actuation means is required for attraction of the beads 13.

However, according to a further embodiment of the invention, additional external magnetic fields may be applied to the sensor device 15 as described in the former embodiment for e.g. realising a still faster attraction of magnetic particles or beads 13 from the bulk toward the binding surface 40 or for stirring. An additional external magnetic field with low gradient, however, does not realise the force required for attracting the magnetic particles or beads 13 close to the binding surface 40. Preferably, AC fields may be used for these additional external magnetic fields. DC fields, which may originate from e.g. permanent magnets, will shift the R(H) resistance change characteristic from the magnetic sensor element 23 and introduce gain variations. On the contrary, AC fields will only introduce additional frequency components, which may or may not interfere with the detection mechanism and may or may not introduce gain errors. Therefore, preferably AC fields may be used which have a frequency such that the detection mechanism is not affected. Furthermore, the attack and decay of the envelope of such additional external magnetic fields should be relatively slow compared to the actual frequency in order to not generate magnetic build-up in the sensor 10. Abrupt switching of magnetic fields will introduce remnant magnetic fields in the sensor. By slowly increasing and decreasing the amplitude, this effect may be avoided.

In another embodiment of the present invention, the magnetic particle or bead attraction-detection mechanism may be implemented locally and time-sequentially on a multi-sensor biochip, comprising a plurality of sensor devices 15. Each time a sensor device 15 on the chip is powered or used for the attraction and/or detection of magnetic particles or beads 13, target-bead-antibody combinations bind very tightly on the binding surface 40 of that sensor device 15. In the same time period, the other unused sensor devices 15 on the biochip comprise unspecified loosely bonded magnetic particles or beads 13, which can be washed away easily. In this way each sensor device 15 on the biochip may be used separately, so that the biochip is applicable for continuous or periodic monitoring purposes.

Every time a measurement is performed by one of the sensor devices 15 on the biochip, the unspecified bonded molecules and beads 13 on the other (unused) sensor devices 15 are washed away prior to a next measurement. As a variation, the same sensor device 15 may be used several times, where the tightly bonded beads are not removed but used as a starting (calibration) point for a next measurement.

For sensor devices 15 with a non-uniform sensitivity across the sensor surface 14 the applied magnetic fields should be arranged in a way to give the highest density of bound particles or beads 13 in the high-sensitivity regions of the sensor device 15 (see further).

Hereinabove, calculations of distribution of force have been shown and compared to the areas of highest sensitivity. Magnetic structures, such as individual magnetic particles or multi-particle magnetic structures or magnetic bead chains 10, will be attracted to the binding surface 40 where the particles or beads 13 can be detected by the detector or sensor element 23. According to embodiments of the invention, the attractive force ($F_{magn,z}$) may be strong enough to bring the particles or beads 13 to the sensor surface 14 within a range in the order of nanometers, i.e. in the range of the size of biological molecules the sensor surface 14 may be modified with in order to form the binding surface 40 so as to bind the target molecules present in the fluid to be analysed, which are bound to magnetic particles or beads 13.

For sensor devices 15 with a uniform sensitivity across the binding surface, the surface coverage by magnetic particles or beads 13 should be as uniform as possible, i.e. magnetic structures, such as individual magnetic particles or multi-particle magnetic structures or magnetic bead chains 10, should not be attracted only to the edges of the sensor devices. A uniform particle distribution can be achieved under the following conditions:

The in-plane forces on the particles or beads 13 should be negligible ($F_{magn,x}=F_{magn,y}\approx 0$).

The attractive force on the particles or beads 13 should be uniform across the binding surface 40 ($F_{magn,z}$=constant).

Using equation (1) and the fact that the magnetic moment m is proportional to the applied magnetic field B, it can be found that:

$$\frac{\partial B^2}{\partial x} = \frac{\partial B^2}{\partial y} = 0 \quad (15)$$

and $$\frac{\partial B^2}{\partial z} = \text{const.} \quad (16)$$

with $$B^2 = B_x^2 + B_y^2 + B_z^2 \quad (17)$$

In case of translational symmetry along the y-axis, equations (15) to (17) can be simplified by assuming $B_y=0$ and d/dy=0:

$$\frac{\partial}{\partial x}(B_x^2 + B_z^2) = 0 \quad (18)$$

$$\frac{\partial}{\partial z}(B_x^2 + B_z^2) = \text{const.} \quad (19)$$

and $$\frac{\partial B_x}{\partial x} + \frac{\partial B_z}{\partial z} = 0 \quad (20)$$

wherein equation (20) is derived from Maxwell equation $\nabla B=0$.

Figure 19:
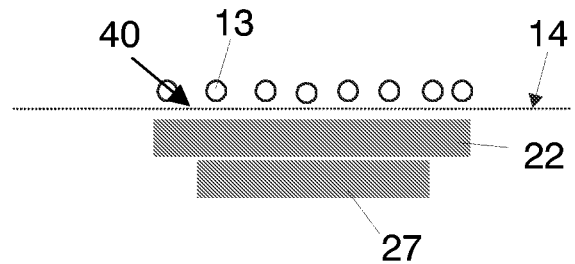
FIGS. 19 and 20 are cross-sectional views of current wires for generating a homogenous particle distribution on the binding surface of a sensor device according to embodiments of the present invention.
Figure 20:
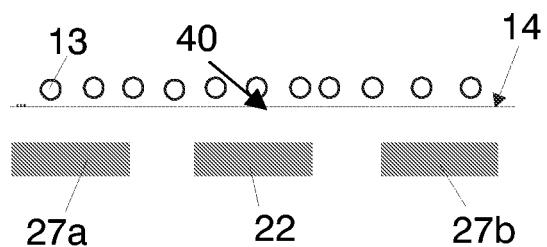

According to embodiments of the present invention, possible arrangements of current wires 22 which may be used according to the present invention to generate such fields which lead to a uniform attraction across the sensor surface 14 are sketched in FIGS. 19 and 20, which show cross-sectional views of possible current wire configurations to generate a homogenous particle distribution on the sensor surface 14 of the sensor device 15. In this figures, the currents in the current wires 22 run in a direction perpendicular to the plane of the paper.

According to embodiments of the invention, the variation of magnetic field gradient in the x-direction (and thus the magnetic force in the x-direction) may be reduced by introducing additional current-wires 27, for example by adding a current wire 27 below the current wire 22 (FIG. 19) or by adding current wires 27a, 27b next to the current wire 22 (FIG. 20). Alternatively added current wires may be a plurality of current wires, a so-called segment of current wires.

In case of FIG. 19, the resulting non-rectangular current distribution can generate a more homogeneous distribution of particles or beads 13 on the binding surface 14 of the sensor device 15 than a single current wire 22 with rectangular cross-section. In the embodiment of FIG. 19, the generated magnetic field is more homogeneous than in an embodiment with a single current wire 22 because the aspect ratio of the current wire combination approaches one. The closer the aspect ratio of the current wire (or current wire combination) is to one, the more homogeneous the generated magnetic field is. The most homogeneous magnetic field would be obtained by a circular current wire, if the binding surface 40 would be circular as well and centered around the current wire. The current wire combinations as shown in FIG. 19 and FIG. 20 can e.g. be used instead of each of the current wires in FIG. 7. Alternatively, the current wire combinations as shown in FIG. 19 and FIG. 20 can e.g. be used per se next to a single magnetic sensor element.

Figure 21:
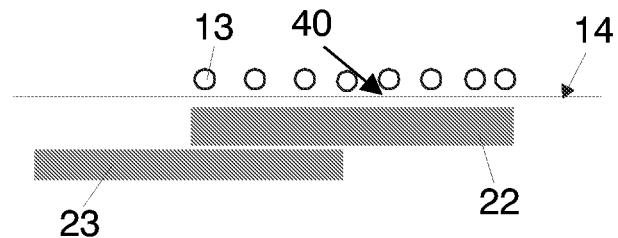
FIG. 21 is a cross-sectional view of a sensor configuration according to an embodiment of the invention.

FIG. 21 shows a current wire 22 which attracts a cluster of particles or beads 13 to the binding surface 14, while the particles or beads 13 are being detected by a sensor element 23. Current wire 22 may have a lower electrical resistance than sensor element 23, so that the current wire 22 is more suited for the generation of magnetic fields.

As explained above with respect to the second aspect of the present invention, an in-plane magnetic field may create in-plane multi-particle magnetic structures or magnetic bead chains 10. These multi-particle magnetic structures or magnetic bead chains 10 may, in some embodiments, be attracted to the sensor surface 14 by magnetic field gradients oriented in a direction substantially perpendicular to the sensor surface 14 induced by, for example, current wires 22 close to the sensor surface 14. The magnetic field gradients induced by current wires 22 may, in the case of a circular current wire 22 and disregarding matrix effects of the surrounding, be essentially axially symmetrical. This means that there is also an in-plane gradient which exerts forces substantially perpendicularly to the axis of the multi-particle magnetic structures or magnetic bead chains 10 at the sensor surface 14. This will lead to a non-homogeneous distribution of the multi-particle magnetic structures or magnetic bead chains 10.

Figure 22:
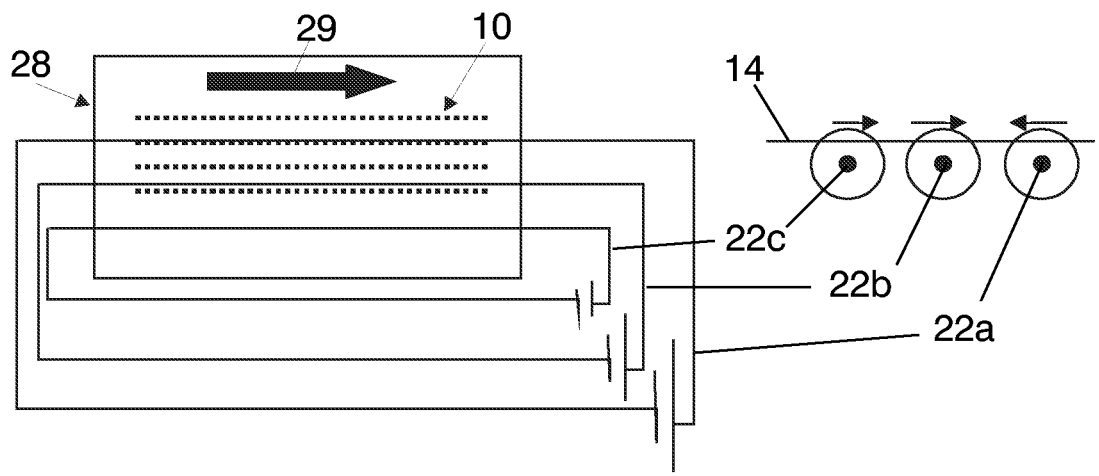
FIG. 22 illustrates in-plane "magnetic wave actuation" of bead columns by an array of current wires which may be addressed sequentially.

The solution for this problem is to use a 1D array 28 of current wires 22a, 22b, 22c and address these current wires 22a, 22b, 22c in a sequential manner. This is illustrated in FIG. 22. The right hand part of this drawing shows a cross-section of the array 28 of current wires 22a, 22b, 22c. The in-plane gradient is varied. The multi-particle magnetic structures or magnetic bead chains 10 are rolling over the sensor surface 14 in order to create a continuous rolling motion and in this way improve the binding kinetics as all parts of the multi-particle magnetic structures or magnetic bead chains 10 get in close contact with the binding surface 40 in this rolling motion. The main direction of the magnetic field is indicated by arrow 29.

A further embodiment according to the present invention is an advantageous combination of the first and second embodiments. Magneto-resistive sensors elements 23, for example, are sensitive to in-plane fields. In case large fields are needed for particle manipulation, these are preferably applied out-of-plane.

Figure 23:
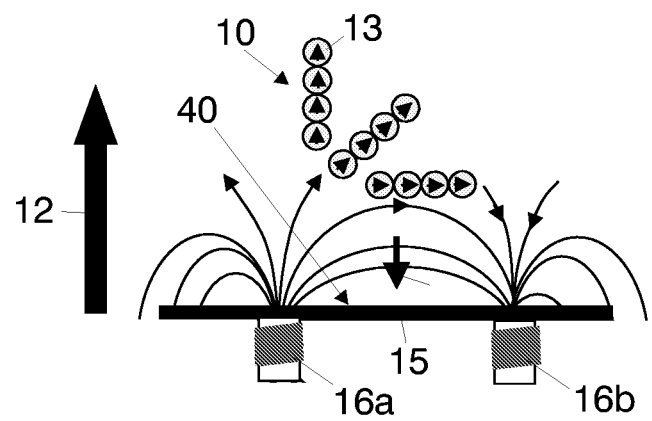
FIG. 23 is a cross-sectional view of a sensor configuration according to an embodiment of the invention.

In this embodiment the magnetic fields required for the process step 'attracting' are applied out-of-plane. Thereafter the direction of the magnetic field is changed toward an in-plane direction for the process step 'binding' (as in the second embodiment). Preferably, the applied magnetic field is rotated so as to maintain the chains 10 of beads 13, but reorient them so that their long axis is lying essentially in-plane, in a direction substantially parallel to the surface 14 of the sensor device 15. An example is sketched in FIG. 23, which shows a sensor device 15 and two external magnetic field gradient generating means, in the example given two external coils 16a, 16b. By using two coils 16a, 16b, an in-plane magnetic field may be induced causing the multi-particle magnetic structures or magnetic bead chains 10 of particles or beads 13 (formed in an externally applied out-of-plane field) to rotate and lie flat with respect to the binding surface 40. The magnetic field gradient attracts the multi-particle magnetic structures or magnetic bead chains 10 to the sensor surface 14 of the sensor device 15.

Figure 24:
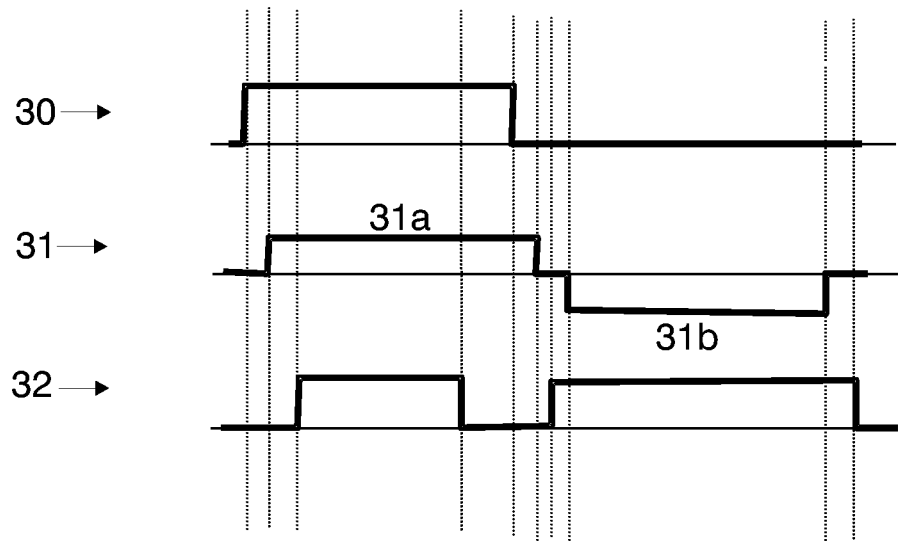
FIG. 24 is an example of excitation sequences as a function of time according to an embodiment of the invention.

In other embodiments according to the present invention, uniform external fields, non-uniform external fields or on-chip current wires may be used to actuate the magnetic particles 13. FIG. 24 illustrates examples of sequences of signals to drive the different field-generating means. Curve 30 illustrates on-chip currents in current wires 22a, 22b for the attraction of magnetic particles or beads 13 toward the sensor surface 14. Curve 31 illustrates the excitation sequence of a small external coil. Part 31a of curve 31 represents the attraction of the beads from the bulk to the sensor surface 14 and part 31b represents the repelling force into the bulk. Curve 32 illustrates the excitation sequence for a large coil to magnetise the particles or beads 13 and form columns or chains 10.

The present invention has been described mainly by using magneto-resistive sensors 23 for the detection of magnetic particles or beads 13. It has, however, to be noted that the beads 13 may also be detected by other magnetic sensor means, such as, for example, with Hall sensors, coils, etc.

As earlier described, in embodiments according to this present invention, enhanced rotation of the beads 13 can also used to improve the speed of the 'binding' step.

The second aspect of the present invention shows different advantages. Due to the larger volume and resulting larger shear forces, multi-particle structures 10 are more sensitive to fluid washing steps than single particles 13. This may result in more effective washing and less non-specific binding.

Furthermore, gravitational forces may be higher for multi-particle structures 10 than for individual particles 13. The present invention, in the different aspects, has been focused on the use of magnetic forces. However, gravitational forces will need to be corrected for and can be used in advantage (e.g. for the 'attracting' step).

Another advantage of using multi-particle structures in accordance with the second aspect of the invention, is that aggregates 10 of magnetic beads 13 have a larger (collective) magnetic moment and hence can be manipulated using smaller field gradients than those required to manipulate individual beads 13. These magnetic field gradients may, for example, be produced by a magnet or coil placed beneath the sensor device 15 and/or by on-chip current wires 22a, 22b.

Magnetic beads 13, as used in any of the first or second aspects of the invention, can be attracted to a sensor surface 14 from a large volume sample, using magnetic forces alone or in combination with the sedimentation and diffusion processes. Furthermore, chains 10 of magnetic beads 13 in accordance with the second aspect of the invention can be attracted toward the binding surface 40, which locally creates a high bead concentration, a good contact between beads and sensor binding surface 40, and thus an increased binding rate.

The processes of the beads 13 near the sensor surface 14 (e.g. attract, bind, stringency, and their repetitions) can all be measured as a function of time. The data are indicative of the kinetics of the processes. The kinetics depend on the target concentration in the solution, and as such the data can indicate what the target concentration was as soon as the signal appears above the noise. Also, the measurement of kinetics allows the measurement in a large dynamic range, because a high target concentration will be detected very rapidly (e.g. in a few seconds) while low target concentrations can be detected after a much longer processing time (e.g. minutes to hours). Also, the kinetics and noise signals can be analysed as a quality control, to check if the assay has evolved correctly and ensure for the end-user that the test result is reliable.

It is to be understood that although preferred embodiments, specific constructions and configurations, as well as materials, have been discussed herein for devices according to the present invention, various changes or modifications in form and detail may be made without departing from the scope and spirit of this invention. For example, the invention has been described by means of magnetic detection of the magnetic particles 13. The magnetic detection can be done by magnetic sensors integrated in the disposable part (the chip and/or the cartridge) but it has to be understood that the magnetic sensors can also be part of the re-usable reader system (e.g. as a read-head that is brought close to the cartridge). Furthermore, according to the invention, the magnetic particles 13 may also be detected in any other suitable way, e.g. by optical detection means. The optical detector can be part of the disposable (the chip and/or the cartridge) or of the re-usable reader system.

The invention claimed is:

1. A sensor device (15) for detecting magnetic particles (13), the sensor device (15) having a binding surface (40) with binding sites thereon and comprising:
   at least one sensor element (23) for detecting the presence of magnetic particles (13),
   means for attracting magnetic structures toward and onto the binding surface (40) of the sensor device (15), said magnetic structures comprising at least one magnetic particle (13),
   means for re-arranging and randomizing the position of individual magnetic particles (13) with respect to the binding sites on the binding surface (40) to give binding sites on all individual particles (13) a substantial probability to have a contact time with binding sites on the binding surface (40).

2. A sensor device (15) according to claim 1, the magnetic particles (13) being present in sample volume, wherein said means for re-arranging and randomising the position of individual magnetic particles (13) is adapted such that individual magnetic particles (13) are loosened from the binding surface

(40) such that 90% of the individual magnetic particles (13) which are part of a magnetic structure (10) stay within 10% of the sample volume.

3. A sensor device (15) according to claim 1, furthermore comprising field generating means adapted for forming multi-particle magnetic structures (10) having a long axis substantially parallel with the binding surface (40) of the sensor device (15), said multi-particle structures (10) comprising a plurality of individual magnetic particles (13).

4. A sensor device (15) according to claim 3, wherein the field generating means adapted for forming multi-particle magnetic structures (10) is an on-chip or an off-chip magnetic field generating means.

5. A sensor device (15) according to claim 3, wherein the multi-particle structures (10) are chains of magnetic particles.

6. A sensor device (15) according to claim 1, wherein the means for attracting said magnetic structures toward and onto the binding surface (40) of the sensor device (15) is an on-chip or an off-chip means.

7. A sensor device (15) according to claim 6, wherein the means for attracting said magnetic structures toward and onto the binding surface (40) of the sensor device (15) is an on-chip or an off-chip element having a relative permeability larger than one.

8. A sensor device (15) according to claim 7, wherein said on-chip or off-chip element changes position or shape in order to locally vary a generated magnetic field gradient.

9. A method for a biosensing process, the biosensing process comprising detection of magnetic particles (13) by means of a sensor device (15) having a binding surface (40) with binding sites thereon, the method comprising:

attracting magnetic structures comprising at least one magnetic particle (13) toward and onto the binding surface (40) of the sensor device (15), and re-arranging and randomising the position of the individual magnetic particles (13) with respect to the binding sites on the binding surface (40) to give binding sites of all said particles (13) a substantial probability to have a contact time with binding sites on the binding surface (40).

10. A method according to claim 9, magnetic particles (13) being present in a sample volume, wherein re-arranging and randomising the position of the individual magnetic particles (13) is such that individual magnetic particles (13) are loosened from the binding surface (40) such that 90% of the particles (13) stays within 10% of the sample volume.

11. A method according to claim 9, furthermore comprising applying a magnetic field adapted for forming multi-particle magnetic structures (10) having a long axis substantially parallel with the binding surface (40) of the sensor device (15), said multi-particle magnetic structures (10) comprising a plurality of individual magnetic particles (13).

12. A method according to claim 11, wherein applying a magnetic field is performed by applying a chain forming magnetic field for forming chains (10) of magnetic particles.

13. A method according to claim 9, wherein attracting said magnetic structures toward and onto the binding surface (40) is performed by applying an on-chip or an off-chip magnetic field.

* * * * *